United States Patent [19]
Ozawa et al.

[11] Patent Number: 5,988,857
[45] Date of Patent: Nov. 23, 1999

[54] AUTOMATIC PROCESSING SYSTEM

[75] Inventors: Satoshi Ozawa, Musashino; Kootaroo Yamashita, Hachiouji; Yuji Miyahara, Kodaira; Toshiyuki Ikeda, Hitachinaka, all of Japan

[73] Assignee: Hitachi, Ltd., Tokyo, Japan

[21] Appl. No.: 08/916,667

[22] Filed: Aug. 22, 1997

[30] Foreign Application Priority Data

Aug. 23, 1996 [JP] Japan ................................. 8-222071

[51] Int. Cl.⁶ .............................. G06F 19/00; G06G 7/66
[52] U.S. Cl. ................ 364/478.01; 510/161; 198/346.1
[58] Field of Search ........................ 364/478.01; 73/1.87, 73/1.01, 1.02, 32, 53.01; 422/72, 68.1, 50; 375/404, 392; 436/177, 174, 63, 45; 494/37; 210/780, 781; 510/161; 198/346.1

[56] References Cited

U.S. PATENT DOCUMENTS

| | | | |
|---|---|---|---|
| 4,052,164 | 10/1977 | König | 422/72 |
| 4,169,060 | 9/1979 | Columbus | 210/516 |
| 4,740,472 | 4/1988 | Burtis et al. | 436/63 |
| 4,847,205 | 7/1989 | Burtis et al. | 436/45 |
| 4,999,304 | 3/1991 | Robertson | 436/45 |
| 5,045,453 | 9/1991 | Katopodis | 435/18 |
| 5,166,889 | 11/1992 | Cloyd | 702/22 |
| 5,186,844 | 2/1993 | Burd et al. | 210/782 |
| 5,308,506 | 5/1994 | McEwen et al. | 210/745 |
| 5,316,726 | 5/1994 | Babson et al. | 422/65 |

Primary Examiner—William Grant
Assistant Examiner—Mc Dieunel Marc
Attorney, Agent, or Firm—Antonelli, Terry, Stout & Kraus, LLP

[57] ABSTRACT

An automatic processing system and method which has high flexibility, extendibility and failure resistance. An automatic processing system and method that provides for the decentralized control of processings of plural samples. The invention combines a plurality of processing instruments and makes use of sample containers for each sample. Each sample container includes an information processing mechanism, a memory mechanism and a communication mechanism. The sample container has stored therein an abstract processing procedure, and determines, based on information concerning the processing instruments obtained from the processing instruments and the abstract processing procedure, a processing procedure for processing the sample. Thereafter, the processing instruments process the sample based on the processing procedure determined by the sample container. The processing procedure of each sample container can allow for performing priority, and cooperative and concerted operations among the processing instruments and the sample containers.

34 Claims, 10 Drawing Sheets

FIG. 3

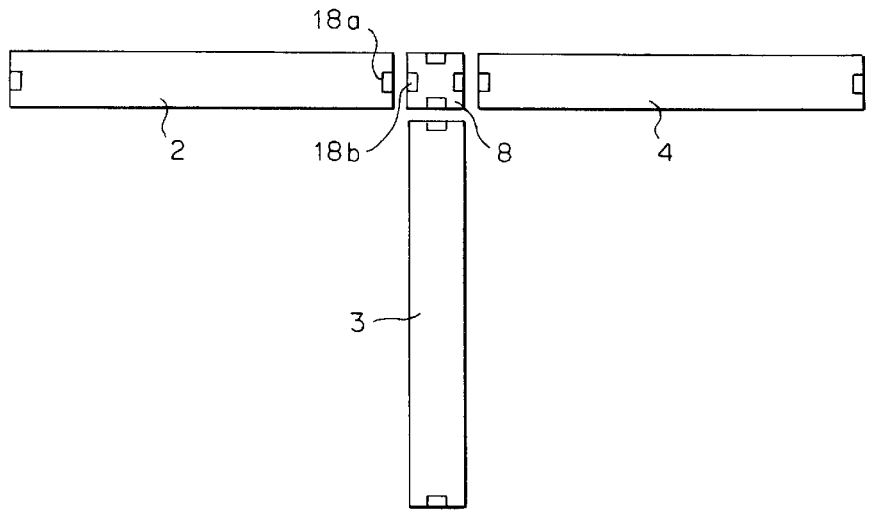

FIG. 4

| INSTRUMENT | INDIVIDUAL IDENTIFICATION INFORMATION | | |
|---|---|---|---|
| | ID NUMBER | TYPE CODE | OTHER INFO. |
| ACCEPTING INSTRUMENT 1 | 1 | ACS.PRC.HCLAS | ... |
| TWO-WAY DELIVERY INSTRUMENT 2 | 2 | 2.DEL.PRC.HCLAS | ... |
| TWO-WAY DELIVERY INSTRUMENT 3 | 3 | 2.DEL.PRC.HCLAS | ... |
| TWO-WAY DELIVERY INSTRUMENT 4 | 4 | 2.DEL.PRC.HCLAS | ... |
| TWO-WAY DELIVERY INSTRUMENT 5 | 5 | 2.DEL.PRC.HCLAS | ... |
| TWO-WAY DELIVERY INSTRUMENT 6 | 6 | 2.DEL.PRC.HCLAS | ... |
| TWO-WAY DELIVERY INSTRUMENT 7 | 7 | 2.DEL.PRC.HCLAS | ... |
| FOUR-WAY DELIVERY INSTRUMENT 8 | 8 | 4.DEL.PRC.HCLAS | ... |
| FOUR-WAY DELIVERY INSTRUMENT 9 | 9 | 4.DEL.PRC.HCLAS | ... |
| CENTRIFUGE INSTRUMENT 10 | 10 | CEN.PRC.HCLAS | ... |
| ALIQUOTING INSTRUMENT 11 | 11 | ALQ.PRC.HCLAS | ... |
| ANALYSIS INSTRUMENT 12 | 12 | 911.ANL.PRC.HCLAS | ... |
| ANALYSIS INSTRUMENT 13 | 13 | 911.ANL.PRC.HCLAS | ... |
| STOCKING INSTRUMENT 14 | 14 | STK.PRC.HCLAS | ... |
| SAMPLE CONTAINER 15 | 15 | 1.CON.HCLAS | ... |

FIG. 5

| CONNECTION SITE | STATE OF CONNECTION | INDIVIDUAL IDENTIFICATION INFORMATION OF THE CONNECTED OBJECT | | |
|---|---|---|---|---|
| | | ID NUMBER | TYPE CODE | OTHER INFORMATION |
| 1 (LEFT SIDE) | CONNECTED | 1 | ACS. PRC. HCLAS | ... |
| 2 (RIGHT SIDE) | CONNECTED | 8 | 4. DEL. PRC. HCLAS | ... |
| ... | | | | |

FIG. 6

| CONNECTION SITE | STATE OF CONNECTION | INDIVIDUAL IDENTIFICATION INFORMATION OF THE CONNECTED OBJECT | | |
|---|---|---|---|---|
| | | ID NUMBER | TYPE CODE | OTHER INFORMATION |
| 1 (LEFT SIDE) | CONNECTED | 2 | 2. DEL. PRC. HCLAS | ... |
| 2 (LOWER SIDE) | CONNECTED | 3 | 2. DEL. PRC. HCLAS | ... |
| 3 (RIGHT SIDE) | CONNECTED | 4 | 2. DEL. PRC. HCLAS | ... |
| 4 (UPPER SIDE) | NOT CONNECTED | – | – | – |
| ... | | | | |

FIG. 7

| LEVEL | CONNECTION SITE | STATE OF CONNECTION | INDIVIDUAL IDENTIFICATION INFORMATION OF THE CONNECTED OBJECT | | |
|---|---|---|---|---|---|
| | | | ID NUMBER | TYPE CODE | OTHER INFORMATION |
| 1 (NEXT) | 1 (LEFT SIDE) | CONNECTED | 1 | ACS.PRC.HCLAS | ... |
| | 2 (RIGHT SIDE) ... | CONNECTED | 8 | 4.DEL.PRC.HCLAS | ... |
| 2 (NEXT OF NEXT) | 1-1 (TOP FACE) ... | CONNECTED | 15 | 1.CON.HCLAS | – |
| | 2-1 (LEFT SIDE) | CONNECTED | 2 | 2.DEL.PRC.HCLAS | ... |
| | 2-2 (LOWER SIDE) | CONNECTED | 3 | 2.DEL.PRC.HCLAS | ... |
| | 2-3 (RIGHT SIDE) | CONNECTED | 4 | 2.DEL.PRC.HCLAS | ... |
| | 2-4 (UPPER SIDE) ... | NOT CONNECTED | – | – | – |

FIG. 8

| LEVEL | CONNECTION SITE | STATE OF CONNECTION | INDIVIDUAL IDENTIFICATION INFORMATION OF THE CONNECTED OBJECT | | |
|---|---|---|---|---|---|
| | | | ID NUMBER | TYPE CODE | OTHER INFORMATION |
| 1 (NEXT) | 1 (LEFT SIDE) | CONNECTED | 2 | 2.DEL.PRC.HCLAS | ... |
| | 2 (LOWER SIDE) | CONNECTED | 3 | 2.DEL.PRC.HCLAS | ... |
| | 3 (RIGHT SIDE) | CONNECTED | 4 | 2.DEL.PRC.HCLAS | ... |
| | 4 (UPPER SIDE) ... | NOT CONNECTED | – | – | – |
| 2 (NEXT OF NEXT) | 1-1 (LEFT SIDE) | CONNECTED | 1 | ACS.PRC.HCLAS | ... |
| | 1-2 (RIGHT SIDE) ... | CONNECTED | 8 | 4.DEL.PRC.HCLAS | ... |
| | 2-1 (LOWER SIDE) | NOT CONNECTED | – | – | – |
| | 2-2 (UPPER SIDE) | CONNECTED | 8 | 4.DEL.PRC.HCLAS | ... |
| | 2-3 (RIGHT SIDE) ... | CONNECTED | 12 | 911.ANL.PRC.HCLAS | ... |
| | 3-1 (LEFT SIDE) | CONNECTED | 8 | 4.DEL.PRC.HCLAS | ... |
| | 3-2 (RIGHT SIDE) ... | CONNECTED | 10 | CEN.PRC.HCLAS | ... |
| | ... | | | | |

FIG. 9

| ID NUMBER OF SAMPLE CONTAINER MODULE | 15 |
|---|---|
| IDENTIFICATION CODE OF SAMPLE AND REQUESTER | 960229.PT3333.DR222 |
| KIND AND FORM OF SAMPLE | WHOLE BLOOD, CAPPED TEST TUBE |
| DATE AND TIME OF RECEPTION | 9:20, FEB. 29, 1996 |
| URGENCY | 3 |
| DEADLINE | 10:20, FEB. 29, 1996 |
| NUMBER OF REQUESTED ITEMS TO BE ANALYZED | 6 |

| LIST OF REQUESTED ITEMS TO BE ANALYZED AND | ABSTRACT PROCESSING PROCEDURE |
|---|---|
| BUN | CEN.ALQ. >.ANL |
| GOT | CEN.ALQ. >.ANL |
| GPT | CEN.ALQ. >.ANL |
| Na | CEN.ALQ. >.ANL |
| K | CEN.ALQ. >.ANL |
| Cl | CEN.ALQ. >.ANL |

FIG. 10

| ID NUMBER OF SAMPLE CONTAINER MODULE | 19 |
|---|---|
| IDENTIFICATION CODE OF SAMPLE AND REQUESTER | 960229.PT3333.DR222 |
| KIND AND FORM OF SAMPLE | BLOOD SERUM UPCAPPED TEST TUBE |
| DATE AND TIME OF RECEPTION | 9:20, FEB. 29, 1996 |
| URGENCY | 3 |
| DEADLINE | 10:20, FEB. 29, 1996 |
| NUMBER OF REQUESTED ITEMS TO BE ANALYZED | 6 |

| LIST OF REQUESTED ITEMS TO BE ANALYZED AND | ABSTRACT PROCESSING PROCEDURE |
|---|---|
| BUN | ANL |
| GOT | ANL |
| GPT | ANL |
| Na | ANL |
| K | ANL |
| Cl | ANL |

FIG. 20

| ID NUMBER OF SAMPLE CONTAINER MODULE | 19 |
|---|---|
| IDENTIFICATION CODE OF SAMPLE AND REQUESTER | 960229. PT3333. DR222 |
| KIND AND FORM OF SAMPLE | BLOOD SERUM, UNCAPPED TEST TUBE |
| DATE AND TIME OF RECEPTION | 9:20, Feb. 29, 1996 |
| URGENCY | 3 |
| DEADLINE | 10:20, Feb. 29, 1996 |
| NUMBER OF REQUESTED ITEMS TO BE ANALYZED | 6 |

| LIST OF REQUESTED ITEMS TO BE ANALYZED AND | ABSTRACT PROCESSING PROCEDURE |
|---|---|
| BUN | ANL |
| GOT | ANL |
| GPT | ANL |
| Na | ANL |
| K | ANL |
| Cl | ANL |

FIG. 21

| ID NUMBER OF SAMPLE CONTAINER MODULE | 19 |
|---|---|
| IDENTIFICATION CODE OF SAMPLE AND REQUESTER | 960229.PT3333.DR222.CON15 |
| KIND AND FORM OF SAMPLE | BLOOD SERUM, UNCAPPED TEST TUBE |
| DATE AND TIME OF RECEPTION | 9:20, Feb. 29, 1996 |
| URGENCY | 3 |
| DEADLINE | 10:20, Feb. 29, 1996 |
| NUMBER OF REQUESTED ITEMS TO BE ANALYZED | 6 |

| LIST OF REQUESTED ITEMS TO BE ANALYZED AND | ABSTRACT PROCESSING PROCEDURE |
|---|---|
| BUN | ANL |
| GOT | ANL |
| GPT | ANL |
| Na | ANL |
| K | ANL |
| Cl | ANL |

AUTOMATIC PROCESSING SYSTEM

BACKGROUND OF THE INVENTION

The present invention relates to an automatic processing system. More particularly, the present invention relates to an automatic processing system which is equipped with sample delivering instruments among analyzing systems, centrifuging instruments and aliquoting instruments for analyzing samples such as blood or urine.

In an automatic processing system equipped with an automatic clinical analyzer or a delivery instrument, there is used a method in which a central processing instrument such as a controller, a personal computer or a work station for controlling those devices is provided so that the operations of the devices may be centrally controlled by the central processing instrument. This method is disclosed, for example, in U.S. Pat. No. 5,351,801. In another system, the individual devices are not directly controlled by the central processing instrument but indirectly by providing an intermediate controller at an intermediate stage. This intermediate controller is controlled by the central processing instrument. Thus, the operations of the individual devices are substantially defined by the central processing instrument. Therefore, this method is also understood to be in the central control mode.

In Japanese Utility Model Laid-Open No. 112956/1982, there is disclosed. a method of analyzing a sample according to printing on the sample container. Such printing includes data such as identification information of the items to be analyzed in the form of bar codes. The system reads the data when the sample container is set in the system, and analyzes the sample by the central processing instrument on the basis of the information. The aforementioned existing automatic processing system according to the central control method has the following problems.

When the system is to be constructed, it is necessary to develop software for controlling the central processing instrument in accordance with the individual system arrangements. It is both tedious and expensive to develop the controlling softwares individually.

Moreover, the control software has to be changed when a part of the instruments in the system are to be replaced by other instruments or added or removed, when the layout is to be changed or when the delivery route of the sample container is to be changed. Another problem is that it is both time consuming and expensive to design, code, install, verify or debug the software and to document, explain and learn how to use the method.

In particular, since a series of analysis has to be urgently carried out in the field of clinical diagnosis it is problematic if the control software requires changing. Because this necessitates the system to be halted in the case of the central control method. Another problem arises when the control software is erroneously designed and/or coded so that the time period for halting the system is increased.

During operation, a trouble at a portion of the system influences the entire system if part of the instrument malfunctions, if the reliability of the measured value is so low that the analysis has to be retried, if the reagent is exhausted to require its replacement, if the sensor is worn out to require its replacement, or if a part of the instrument is halted for its maintenance. Another problem is that it is particularly troublesome to design control software which can cope on real time with the emergent situations of all the instruments of the system.

According to Japan Patent Application 62-226058 a cassette for an automatic analyzer instrument is described. The cassette includes at least one container to hold a sample, a data processor, and a radio communication device. The data processor is capable of storing and retrieving information about the sample in response to commands from external instruments via the radio communication device. The information about the sample includes sample ID, analytical parameters (analytes to be measured), the analyzer to be used and the need to retry the analysis.

An external computer transmits the information to the cassette via the radio communication device, after the cassette is placed on an self-propelled vehicle. The vehicle brings the cassette to the specified analyzer. The analyzer reads the analytical parameters from the cassette via the radio communication device, and performs the analysis. The analytical results are transmitted to the computer which decides whether retry is necessary. If retry is necessary the computer sets the retry flag in the cassette thereby initiating a retry measurement procedure. Thus, it is proposed that the system can flexibly perform the required analytical procedures automatically.

However, the above-described conventional system suffers from numerous disadvantages. One disadvantage of the above-described conventional system is the presence of the external computer that centrally controls the entire system. Additionally, although it is stated that an active function can be given to the cassette, the role of the data processor in the cassette is passive. In other words, it is controlled by the external computer or the analyzer. Thus, the data processor does not act independently.

SUMMARY OF THE INVENTION

An object of the present invention is to provide an automatic processing system which is easy to construct, modify and extend, which can change the arrangement flexibly during operation, which has such a high failure tolerance that it can maximize the ability of the system dynamically for the most appropriate processing.

In order to achieve the above-specified object, the present invention provides a cooperative decentralized system that operates by giving information processing functions individually to the instruments constituting the system to run them autonomously, equipping the individual instruments with a communication mechanism to exchange the information, and equipping the individual instruments with software for cooperative concerted operations.

More particularly, the present invention provides an automatic processing system which includes a plurality of processing instruments and at least one object to be processed by the plurality of processing instruments. Each of the plurality of processing instruments and the object include an information processor, a memory and a communication mechanism. The object determines a processing procedure based on information concerning the processing instruments. The processing instruments process the object based on the processing procedure obtained from the object. For example, the object is a sample container containing a sample, and the processing procedure includes at least one of an accepting operation, a temporary stocking operation, a delivery operation, a shunting operation, a storing operation, a centrifuging operation, an uncapping operation, an aliquoting operation, a sample analyzing operation, and a processing operation for analysis.

The information, for example, represents an arrangement of the processing instruments. It can also represent the functions of the processing instruments, or the operation schedule for the processing instruments to process the sample container The plurality of processing instruments are classified according to individual functions, and the sample container holds in its memory an abstract processing procedure that is described as the combination of the functions so that the sample container determines the processing procedure based on the abstract processing procedure and the information. The sample container and the processing instruments include connection apparatus, capable of changing their individual states of connection.

Moreover, the processing instruments and the sample container stores in its memory an identification information including an ID number or a model identification code individually. Using this identification information, together with the communication mechanism, communication among the sample container and the processing instruments is enabled. Through the communication mechanism, the sample container acquires the information concerning the processing instruments from the processing instruments. Based on the information, the sample container determines the processing procedure.

Further, information on a predetermined counterpart of communication is acquired through communications with the predetermined counterpart using the communication mechanisms indirectly via the modules in between so that the sample container may determine the processing procedure based on the information acquired.

Still moreover, the sample container stores the information representing the deadline for processing in the memory, and the processing instruments may process the sample container with different priority, depending on the information representing the processing deadline. The processing instruments and the sample containers evaluate their reliabilities mutually, and the sample container selects one of the plural processing instruments based on the evaluation result so that the selected processing instrument may process the sample container or that the plurality of processing instruments may reject the sample container.

Furthermore, a first predetermined sample container may acquire information concerning a processing instrument or another second predetermined sample container, from the other processing instruments or a third predetermined sample container. The latter instruments or the third sample container may act as a proxy for the former instruments or the second sample container.

BRIEF DESCRIPTION OF THE DRAWINGS

The present invention will be more apparent from the following detailed description, when taken in conjunction with the accompanying drawings, in which:

FIG. 3 is an enlarged diagram of a portion of FIG. 1;

FIG. 4 is a diagram illustrating a schematic table of the individual identification information of the individual modules of the first embodiment;

FIG. 5 is a diagram illustrating the information of the situation of connection to be acquired by the two-way delivery instrument 2;

FIG. 6 is a diagram illustrating the information of the situation of connection to be acquired by the four-way delivery instrument 8;

FIG. 7 is a diagram illustrating the information of the situation of connection to be acquired secondly by the two-way delivery instrument 2;

FIG. 8 is a diagram illustrating information of the situation of connection to be acquired secondly by the four-way delivery instrument 8;

FIG. 9 is a diagram schematically illustrating the request information to be stored in the sample container 15;

FIG. 10 is a diagram schematically illustrating the request information to be stored in the sample container 19;

FIG. 20 is a diagram schematically illustrating the request information to be stored in a sample container 19; and FIG. 21 is a diagram schematically illustrating the request information to be stored in a sample container 19.

DETAILED DESCRIPTION OF THE PREFERRED EMBODIMENTS

The present invention will be detailed in the following in connection with the embodiments.

First Embodiment

Figure 1:
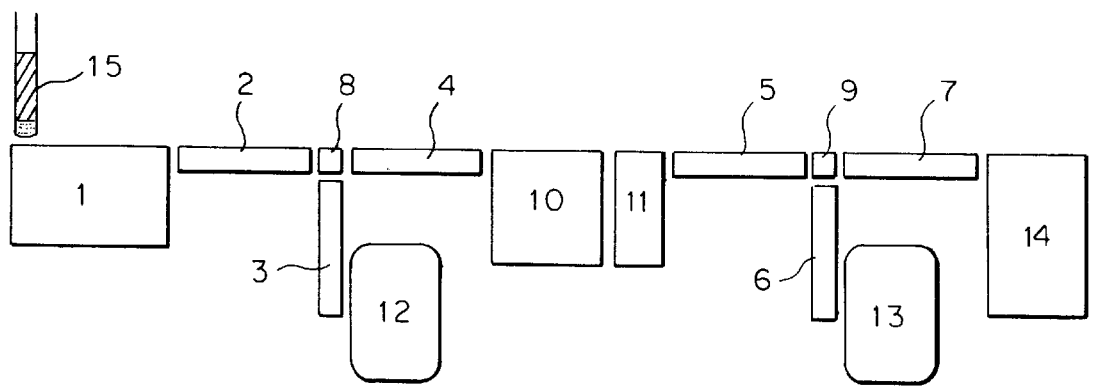
FIG. 1 is a schematic arrangement diagram of an automatic processing system of a first embodiment.

FIG. 1 is a schematic arrangement diagram illustrating a first embodiment of an automatic processing system according to the present invention.

The automatic processing system according to the present invention is constructed to include an accepting instrument 1, two-way delivery instruments 2, 3, 4, 5, 6, and 7, four-way delivery instruments 8 and 9, a centrifuging instrument 10, an aliquoting instrument 11, analysis instruments 12 and 13 and a stocking instrument 14. It should be noted that aliquoting, as used herein, is defined as the dividing or dispensing of portions of a sample. A sample to be analyzed is contained in a sample container 15.

Figure 2:
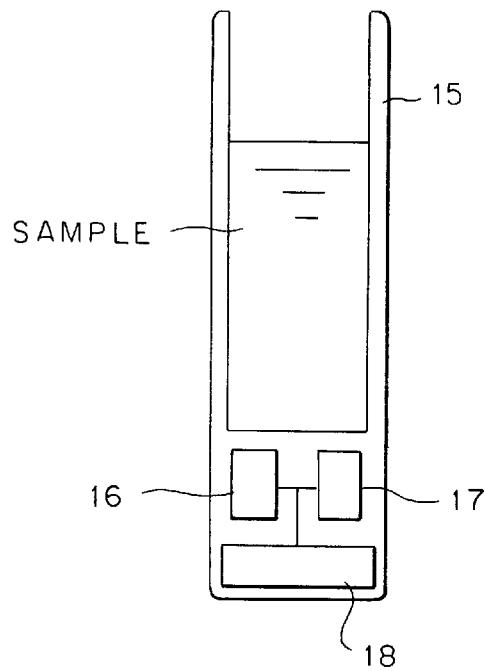
FIG. 2 is a schematic arrangement diagram of a sample container.

FIG. 2 is a schematic arrangement diagram illustrating the sample container 15 of the present embodiment. In the present embodiment, the sample container 15 is equipped with an information processor 16, a memory 17 and a communication mechanism 18. Although the sample is contained directly in the sample container, in FIG. 2, a disposable container such as a cup or a test tube or a reusable container can be interposed between the sample container 15 and the sample so that the sample container 15 can be reused. The information processor 16, the memory 17 and the communication mechanism 18 are integrally formed in the sample container 15, in FIG. 2, but can be independent of the sample container 15 as detachable units so that they can be reused.

Although not shown in FIG. 1, other systems of the present embodiment are equipped like the sample container 15 with the information processor, the memory and the communication mechanism in addition to the processing mechanisms intrinsic to the systems. In the present embodiment, the instruments and the sample container, constituting the automatic processing system, are equipped with the information processor, the memory and the communication mechanism. From this point of view, the individual instruments and the sample container are considered to be in the same category and will be called together "module". In order to clarify the description of the automatic processing system, the individual instruments and the sample container may be called the modules. The modules means various instruments and the sample container, which are equipped with the information processor, the memory and the communication mechanism.

Hereinafter, the operation of the present embodiment will be summarized. As described above, each module of the automatic processing system of the present embodiment is equipped with the information processor, the memory and the communication mechanism. The memory of each module is stored with a software, so that each information processor executes the necessary processings on the basis of the software read out from each memory. The operation of each module is essentially regulated by the algorithm and data, which are expressed in the software stored in the memory of each module. This software is composed of a common portion shared by all modules and a unique portion prepared individually according to the kind and specifications of each module. Any software common among the individual modules need not be redeveloped for the individual modules so that consistency of the operations common among the individual modules can be maintained, which improves the ease of maintenance at the time of updating the common portion. In the present invention, because of the provision of many kinds of instruments (or modules) having the mechanisms intrinsic to the instruments for realizing the different processings such as the aliquoting, analyzing and stocking operations, the software of the intrinsic portions for controlling the operations intrinsic to the individual instruments are individually prepared and are stored in the memory of the module. The storage of the information in the memory of the module may be shortly stated "to store the information in the module" or "to store the module with the information".

In the present invention, on the basis of the software stored in the individual modules, the information processor operates its instruments autonomously so that the individual modules operate autonomously, in a decentralized manner and in a parallel manner. For controlling the individual modules, the automatic processing system of the present invention does not necessarily require a permanent and centralized central processing instrument such as controllers, personal computers, and workstations. Therefore, the system as a whole functions as an autonomous decentralized processing system.

Outside of the automatic processing system, although not shown in FIG. 1, there can be disposed an instrument especially for processing the information, such as a communication terminal of a doctor, a communication terminal of a clinical laboratorian or a communication terminal of a hospital information processing instrument. These communication terminals can be used so that the doctor or clinical laboratorian may perceive the state or operation schedule of the automatic processing system, so that the information of a request for test can be stored in the sample container module, or so that the information of the test result may be extracted and presented to the doctors. These communication terminals are naturally equipped with the information processor and the memory, and can also exchange information with the automatic processing system, when they are equipped, on their instruments or other instruments on the network, with a communication mechanism which is compatible with the communication mechanism of at least one module.

Briefly, the communication terminals and the modules can communicate with each other when all the modules are equipped at least with a compatible communication mechanism and when the communication terminals of the doctor and the clinical laboratorian are equipped with the communication mechanisms made compatible therewith. These communication terminals do not directly control the individual modules, unlike the permanent and centralized central processing instrument of the prior art. Therefore, the communication terminals are not essential for the operation of the system. It will be described in more detail in connection with the following embodiments that the automatic processing system functions as a whole in an autonomous decentralized manner, without any direct participation of those terminals.

As described above, the automatic processing system basically functions as an autonomous decentralized processing system. To determine the operations of the individual modules, however, the information from other modules are secondarily utilized as the material for judgment. Specifically, the information processor executes specific software in the memory so that the communication mechanism of each module is controlled and driven to exchange the information with other modules through the communication mechanism. On the basis of the information (algorithm and/or data) acquired from other modules, each module extends the fundamental operation to perform the extended operation matching the external conditions. The software for this is stored in the memory of each module. As a result, the information from other modules can be secondarily utilized when the operation of each module is to be determined.

Here has been described the case that the information from other modules is reflected on the operation of the module of concern. If a similar mechanism is considered from another point of view, the information from a module may possibly be reflected on the operation of another module. The modules can cooperate and act in concert with each other by their cooperative compensative interactions on the basis of the transfer of the information through the communication mechanism belonging to each module. As a result, the automatic processing system operates in its entirety as the cooperative decentralized processing system. Here will be described in detail the mechanism for causing the modules to cooperate and act in concert with each other.

The automatic processing system of the present invention is a decentralized processing system comprising a group of modules that carry out the process in a decentralized and an autonomous manner, and has no central processing instrument for controlling the entire system. For the adjustment among the modules, and to cause the modules to cooperate and act in concert with each other, each module is equipped with the communication mechanism to exchange information with other modules. On the basis of the information from other modules, each module can perform the cooperative and concerted operation autonomously to effect an efficient operation as the system in its entirety. This cooperative and concerted operation is classified into three stages: the first is to perceive the situation of connection; the second is the contemplated execution; and the third is the long-range optimization. Here will be described in detail the first stage, i.e., the perception of the situation of connection, and the execution that makes use of the cooperative and concerted operation based on the perception in connection with the first to fourth embodiments.

The first connection situation perceiving operation is divided into two kinds according to the types of communication mechanism. The basic one is the communication between adjacent modules, which will be shortly referred to as an adjacent communication mode. A second remote communication mode will be described hereinafter.

<Adjacent Communication Mode>

In the adjacent communication mode, on the basis of the communications with another adjacent module, each module collects information on the state of connection and perceives the state of connection. In order to realize the adjacent communication mode, each module is equipped with a communication mechanism at a section adjacent to another module or at the section to be connected to another module. Each module is stored with the individual identification information (the ID number) and the information such as codes specifying the kind and model of the module (i.e., the instrument or the sample container).

FIG. 3 is an enlarged diagram illustrating a portion of FIG. 1, namely, the connection section between the two-way delivery instruments 2, 3 and 4 and the four-way delivery instrument 8. Each module is equipped with the communication mechanism on its face connectable with another module. The two-way delivery instruments 2, 3 and 4 can be connected at their two ends with other instruments, and the four-way delivery instrument 8 can be connected at its four sides with other instruments and are equipped at its connectable sides with two and four communication mechanisms. These communication mechanisms are shown by small rectangles. Because of the large number, however, the leader lines and numerals are added to only part of the communication mechanisms (18a and 18b) in FIG. 3. The two-way delivery instruments 2, 3 and 4 and the four-way delivery instrument 8 are further equipped at their contact faces (upper faces) with the communication mechanisms so that they can communicate with the communication mechanism 18 at the bottom of the sample container 15 of FIG. 2. Incidentally, this communication mechanism is not shown in FIG. 3.

This communication mechanism is equipped with a transmitting section and a receiving section utilizing infrared rays so that it communicates with the receiving section and the transmitting section of the party of communication by arranging its mechanisms to face the corresponding mechanisms of its communication counterpart. The transmitting section comprises an infrared light emitting diode, a driver circuit and an encoder circuit. The receiving section comprises an infrared photodiode, a receiver circuit and a decoder circuit. The ASIC (Application Specific IC) can also be used in a part of those circuits. Moreover, the UART (Universal Asynchronous Receiver Transmitter) may be provided to control the transmitting mechanism and the receiving mechanism together This UART is equipped with a buffer mechanism for buffering the communication information temporally and a communication control mechanism for controlling the communication protocol.

When the communication with the moving sample container is required as in the two-way delivery instrument or the four-way delivery instrument, the communication is executed at a plurality of positions to locate the position of the sample container by using the infrared light emitting diode array in the transmitting side and the infrared photodiode array on the receiving section. The communication with and the locating of the sample container may be executed by using the photodiode array only in the receiving section and a single light emitting diode of high output power and low directivity on the transmitting section. The optical semiconductor element can be small-sized by using an optical fiber and a light waveguide. In this case, the actual position of the sample container is made to correspond to the individual segments of the light emitting diode array and the photodiode array. By lowering the directivity and enhancing the optical output power and the optical sensitivity thereby, the communication distance can be increased, and the communication can be effected at a plurality of positions by using the pair of single communication mechanisms. The position location can be effected by using a mechanical sensor or the like. Moreover, remote communication between the modules out of contact with each other can be effected by a similar method.

The present embodiment adopts the IrDA standards (the standard on the infrared data communication by Infrared Data Association) as the communication standard. Other well-known techniques can be used as the communication standard. There can be further adopted optical communication means other than infrared such as electric, radiowave, magnetic, electromagnetic, or vibration (sound or ultrasound) communication means.

FIG. 4 is a schematic table showing the individual identification information which is stored in the memory of each module. The individual identification information includes the ID number, the codes (hereinafter referred to as shortly as type codes) specifying the kind and model of the instrument or sample container, and other information. The ID number is exemplified by a serial number but is made identical to the number designating each module for simple description. The type codes are the encoded information representing the name (e.g., HCLAS for the automatic processing system) of the system, whether it is an instrument for processing or an object to be processed such as a sample container (e.g., PRC for an instrument or CON for a sample container), the large classification (e.g., DEL for a delivery instrument and ANL for an analyzing instrument), the small classification (e.g., 2 for a two-way delivery and 4 for a four-way delivery), the model (e.g., 911) and the number (e.g., 1) of samples contained in each container.

Since a plurality of type codes can be defined for each module, there are several ways for expressing and storing the type codes. For example, the instruments are classified according to the hierarchical structure, and the type codes specifying the individual classes are expressed in the order of the hierarchy. As shown in FIG. 4, the type codes are listed in the hierarchy descending order from the right to the left with the separation codes. The type code 911.ANL-.PRC.HCLAS specifies the model 911 instrument belonging to the analyzing instrument class (ANL) of the processing system class (PRC) belonging to the automatic processing system class (HCLAS). In order to show a set of modules belonging to a specific class, only a part of the hierarchical structure may be described as the type code. For example, the type code ANL.PRC.HCLAS specifies a set of instruments belonging to the analyzing instrument class of the processing instrument class belonging to the automatic processing system class. As an example of the other information, the version (e.g., #A15) and variation (e.g., % RS) of the instrument can be combined into #A15. % RS.

The connection situation perceiving operation in the adjacent communication mode is divided into a plurality of steps. At the first step of the connection situation perceiving operation, each module investigates its relation with another adjacent (next) module or another connected module to perceive the situation of connection. The situation of connection, of the first module after the next module at the second step, the second module after the next module at the third step, and so on is sequentially perceived.

At the first step, each module tries to communicate with an adjacent or another connected module through the communication mechanism. If the two modules are physically correctly arranged and connected, the communication between the two modules are effected to establish a communication route, and the site is perceived to be in the connected state at this time, so that this information is stored. If another module is not arranged and connected to the adjacent connection site, the communications at this site are not effected through the communication mechanism to establish no communication route, and that site is perceived to be in the disconnected state at this time, so that this information is stored.

The description will be made in connection with the arrangement shown in FIG. 3. The two-way delivery instrument 2 transmits an infrared signal by using the communication mechanism 18a to try the communication with the opposed four-way delivery instrument 8. This four-way delivery instrument 8 receives the infrared signal by using the communication mechanism 18b to perceive that a module is on the left side of FIG. 3. The four-way delivery instrument 8 transmits the infrared signal by using the communication mechanism 18b. The two-way delivery instrument 2 receives that signal to perceive that a module is on the right side. As a result, a handshake is made between the two modules to establish a communication route, and the two modules perceive that the connection site is in the connected state, so that this information is stored.

Likewise, communication routes are individually established between the two-way delivery instruments 3 and 4 and the four-way delivery instrument 8, and the connected states are perceived. Since no module is present on the upper side of the four-way delivery instrument 8, the trial of communication does not succeed, but it is perceived that it is in the disconnected state, so that this information is stored. When it is necessary to be mechanically correctly connected as in the delivery instruments, the communicable distance between the communication mechanisms 18a and 18b is restricted using a lens, or the optical output or the receiving sensitivity are adjusted and limited. only if correctly connected, the communication route is preferably established, so that the connection site may be perceived to be in the connected state. A module that is not mechanically correctly connected or that in a remote location can be prevented from being judged to be connected.

After the connection has been confirmed, the individual modules exchange messages with each other by using the communication mechanism to acquire and store the information on the situation of connection, that is, the information on what module is connected with the connection side thereby to perceive the situation of connection at the first step.

For example, the two-way delivery instrument 2 uses the communication mechanism 18a to transmit a request message of offering the individual identification information to the four-way delivery instrument 8. This delivery instrument 8 sends a reply message of reporting the individual identification information. This message includes the ID number (8), the type code (4.DEL.PRC.HCLAS) and other information (the column of the four-way delivery instrument 8 of FIG. 4) of the delivery instrument 8. On the basis of this information, the two-way delivery instrument 2 perceives that the module on the right side is the 4 (way delivery instrument) of the DEL (the delivery instrument) of the PRC (processing instrument) belonging to the HCLAS (the automatic processing system), and this information is stored. The four-way delivery instrument 8 likewise perceives the two-way delivery instrument 2, and this information is stored.

Each module executes the aforementioned operations for all the connection sites to acquire whether the individual connection sites are connected or disconnected and the individual identification information on the module in the connected state. For example, FIGS. 5 and 6 shows the connection situations to be acquired and stored by the two-way delivery instrument 2 and the four-way delivery instrument 8 of FIG. 3. Thus, each module can perceive the situation of connection (the arrangement and the individual identification information of the modules) of other adjacent modules.

At the second step of the connection situation perceiving operation, each module exchanges messages with the module in the connected state, so that the information on the module next to the module in the connected state is acquired. Specifically, each module requests the module in the connected state to offer the information on the situation of connection, receives the reply message of the connection situation information and stores the result. Each module can perceive what module is connected to the module in the connected state, i.e., the next to the next of itself.

In FIG. 3, the two-way delivery instrument 2 transmits at first a request message of offering the connection situation information to the four-way delivery instrument 8. In response to this, the four-way delivery instrument 8 sends a reply message of the connection situation information. This connection situation information is the presence/absence of connection and the individual identification information of the modules connected at each connection site of the four-way delivery instrument 8 obtained at the first step. The content of the reply message of the connection situation information sent by the four-way delivery instrument 8 is shown in FIG. 6. In response to the message from the four-way delivery instrument 8, the two-way delivery instrument 2 can perceive and store to which connection site of the addressee it is connected and can perceive and store what module is connected over the four-way delivery instrument 8, i.e., the next to the next.

Likewise, other modules 2, 3, 4, 8 and so on can acquire the information of the situation of connection of the next to the next. The information on the situation of connection of up to the next to the next acquired through the operations, which have been described, by the two-way delivery instrument 2 and the four-way delivery instrument 8 are respectively shown in FIGS. 7 and 8.

By repeating the connection situation perceiving operation, succeedingly, it is possible to perceive the arrangement and the individual identification information of all the modules constituting the system.

In the description thus far made, each communication mechanism utilizes the adjacent communication mode, or the communication between two modules connected with each other through a connection site. However, if each module is equipped with one or more communication mechanism, this communication mechanism can also be controlled by the information processor to execute an extended communication mechanism (or the extended adjacent communication mode). In this extended adjacent communication modes the communication with the module which is not directly in the connected state but separated by the other modules in between is executed. When a message is transmitted, the individual identification information such as the ID number or the type code is utilized as the address information so as to specify the module of the sender and the module of the addressee.

For example, the communication content (or the main text), the sender address information, the addressee address information, the transfer history information, the message ID, the sending time and the validation limit are transmitted. The ID number of the sender module is used as the sender address information; the ID number, the type code or the path information of the addressee module is used as the addressee address information; and at the sending time the ID number of the sender module is used as the transfer history information. The path information will be described hereinafter.

When a module receives a message, its ID number is added to the transfer history information of the message in accordance with a predetermined rule thereby to record that it participated in the transfer of the message. Next, the message is transferred to all the modules in the connected state, except for the later-described exceptions. In order to raise the efficiency, the transfer from the communication mechanism having received the message may be omitted.

When the addressee address information of the received message contains the ID number or the type code of the module, it is judged that the module is one of the addressee of the message, and a collation is made with the list of the reception record (the message ID or the sending time) of the past message. If that message is not present in the reception record, it is judged that the message is one having newly arrived, and the message ID and the sending time are added to the reception record.

Next, the received message is processed, and a reply message is replied, if necessary. The ID number of the module is used as the sender address information and the transfer history information of the reply message, and the sender ID number of the received message is used as the addressee address information. When the communication mechanism for sending the reply message is to be selected, the communication mechanism facing the module of the latest ID number added to the transfer history information is selected with reference to the transfer history information of the received message. As a result, the reply can be efficiently made in the direction of the reception route.

It is further possible to make communication in which not only the ID number and the type code but also the path information are specified as the addressee address information. The message is sent for reply while going back through the path (the transfer history information) through which the received message has been transferred. This makes it possible to specify the path of reply easily thereby to improve the communication efficiency.

As the addition rule of the transfer history information, the separation codes and the ID numbers of the modules having participated in the transfer are added before (on left side of) the original transfer history information. As the path information, likewise, the separation code and the ID number of the module on the transfer path are added after the ID number of the sender module, and the separation code and ID number of the addressee module are added to the last.

Specific description will be made in connection with the system arrangement of FIG. 1. When the message transmitted from the module 1 reaches the module 10 through the modules 2, 8 and 4, the transfer history information is 10.4.8.2.1. This can be simply used as the path information 10.4.8.2.1 to serve as the addressee address information specifying the transfer path of the reply message from the module 10 to the module 1. This is the reversal of the transfer path of the received message.

The modules 4, 8 and 2 existing in the transfer path can refer to this transfer path to judge what adjacent module the message is to be transferred to thereby limit the communication mechanism to be used. This makes it possible to improve the communication efficiency. When the module 8 receives and transfers the reply message to the next, for example, it judges that by transferring the message only to the module 2 positioned next to the module 8 in the addressee address information, the reply message can finally reach the module 1, and transfers the reply message to the module 2 by using only the communication mechanism 18$b$ (shown in FIG. 3) connected with the module 2. The reply message is not transferred from the communication mechanism in other connection sites. As a result, no transfer is made in the direction of the module 3, for example, so that the efficiency can be enhanced.

This is an example of the exception to the otherwise multidirectional principle of the transfer. Specifically, if the path information is used as the addressee address information of the message, the message is transferred only in the direction along the path but not in the other directions.

Other exceptional cases that the received message is not transferred include the case that the ID number is contained in the transfer history information, the case that it can be deemed that the module has already participated in the transfer of the message and the message is transferred doubly or circulatively caused by the splitting and joining of the path, the case that it can be deemed that the message has a deficient content and is invalid, the case that the addressee module is exchanged and removed out of the system, or the case that the validation term of the message has expired and the message need not be transferred. If the message is invalid or if the addressee module is exchanged so that it is decided to quit the transfer, a message of quitting the transfer is sent to the sender.

The module having received a message sends a message of the acknowledgement of reception including the recitation of the received message to the sender module before a reply to the message so as to report the reception of the message. However, reception is not made if the received message is an acknowledgement of reception. The sending module can confirm whether or not the message has arrived at the counterpart based on the message of acknowledgement of reception. If the message fails to arrive, an error processing corresponding to the situation such as a retry sending or a reconfirmation of the situation of connection is executed. Here will be made no description of the acknowledgment of reception so as to explain the communication content (the main text).

In the extended adjacent communication mode, as described above, communications can be executed between remote modules by using the addressee address information. This mode can be executed after the situation of connection of all the modules constituting the system has been perceived in advance by using the aforementioned adjacent communication mode. After the end of the connection situation perceiving operation of the adjacent communication mode, the ID numbers of the adjacent modules next to a module, next to the next and so on may be sequentially perceived to widen the connection situation perceiving range thereby to extend the communicable range.

If it is desired to know whether or not a predetermined kind of module is connected with the system, the extended adjacent communication mode can be used to search the module and thereby to acquire the ID number and the path information. This connection of the module with the system will be referred to briefly as participation.

Here will be explained the case that after each module of the arrangement of FIG. 1 executes the first step of the connection situation perceiving operation to perceive the situation of connection between the module and a module in the connected state, and the accepting instrument 1 searches whether or not the centrifuge instrument 10 is participating in the system. The message is prepared by setting the ID number 1 of the module as the sender address information, the type code CEN of the addressee module as the addressee address information, and the ID number 1 of the module as the transfer history information to the message ID, the sending time and the communication content (e.g., the request message to request to provide the individual identification information). This message is sent from all the communication mechanisms of the module. This message is transferred by the individual modules and reaches the centrifuge instrument 10.

The centrifuge instrument 10 recognizes that the addressee address information (CEN) of the message conforms to the large classification (the centrifuge instrument CEN) of the instrument to which it belongs, and receives the message. The transfer history information of the message is 10.4.8.2.1. Next, the centrifuge instrument 10 transfers the message by using the communication mechanisms other than the mechanism having received that message. If there is any other centrifuge instrument conforming to CEN and participating in the system it will act similarly. From the communication mechanism having received the message, the message of the acknowledgment of reception is sent for reply to the accepting instrument 1, or the sending module. Next, the centrifuge instrument 10 sends the reply message of the individual identification information to the accepting instrument 1.

The accepting instrument 1 can perceive from the message of the acknowledge of reception that the centrifuge instrument 10 participates in the system. The number of centrifuge instruments participating in the system can be perceived from the number of the senders of the acknowledgment of reception. It can be perceived from the sender address information of the acknowledgment of reception that the ID number of the centrifuge instrument 10 is 10, and it can be perceived from the transfer history information that the path information to the centrifuge instrument 10 is 1.2.8.4.10. By storing the information, the communication mode specifying the path information as the addressee address information can be adopted in the communication with the centrifuge instrument 10, so that the efficiency is improved. Moreover, it is possible to perceive the instrument ID of the modules interposed between the module and the centrifuge instrument 10 and the path information. From the individual identification information, moreover, the detail of the centrifuge instrument 10 can be perceived. By requesting to offer the connection situation information, moreover, the situation of connection of the centrifuge instrument 10 can be perceived from the reply message. Thus, by the extended adjacent communication mode it is possible to search whether or not a predetermined module is participating in the system, and it is also possible to acquire the path to the module.

The adjacent communication mode and the extended adjacent communication mode can realize the communication of high level at a low cost with a simple arrangement. By the remote communication mode using infrared rays, the modules can be easily mounted/demounted to construct, modify and extend the system with ease.

Here will be described the case that the second communication mode, or the remote communication mode is used in the connection situation perceiving operation. As the communication mechanism, there can be adopted the system which is equipped with a communication network of higher level. Through a communication network such as the Ethernet, for example, not only the adjacent modules but also the remote modules can directly communicate with each other. In this case, too, it is desirable to perceive by the operation similar to that of the adjacent communication mode whether or not the two modules are correctly arranged and connected with each other. Once the situation of connection with the adjacent module is perceived, at the steps of perceiving the situation of connection with a remote module and the situation of connection of the entirety, the message is exchanged directly remotely to perceive the situation of connections among the remote modules and the entire system easily at a high speed.

These connection situation perceiving operations are desirably performed as one of startup operation at the power-on time or resetting time of each module or at the time of change to the automatic operation mode by canceling the manual operation mode or temporal halt mode. Alternatively, the connection situation perceiving operations may be carried out as one of periodic interrupt processes. Furthermore, the connection situation perceiving operations may also be carried out when a sensor for mechanically detecting the connection/disconnection between modules is provided to detect the situation of connection according to the signal from the sensor, when it is questionable that the situation of connection has been changed due to an abnormal situation such as a communication error, or when a caution message of the change of the situation of connection is received from another module. By this connection situation perceiving operation performed at an interval of other operations or performed when the situation change is presumed, the situation of connection can be perceived on real time and the arrangement of the system can be perceived dynamically.

The connection situation perceiving operations thus far described are realized together with the autonomous operations of the individual modules by the cooperative operation of exchanging the information with each other, and the central processing instrument is not needed. Thanks to the autonomous decentralized processing of the connection situation perceiving operations, the present system can effect a self organization.

On the basis of the connection situation perceiving operation, here will be described the executions such as the delivery and analysis utilizing the ability to carry out the cooperative and concerted operation.

The memory of the sample container is stored, as to the sample specimen in the sample container, with the identification symbol of a patient or requester, the kind of the sample, the list of requested items to be analyzed, the request information such as the deadline by which the analysis result is submitted and the urgency, and an abstract processing procedure on each items to be analyzed.

The request information is written in a request sheet or the communication terminal of the doctor by the doctor or a nurse instructed by the doctor when the sample specimen is sampled from a patient and contained in the sample container. The request sheet is read out by a request sheet reader and converted into electric information, which is inputted to the terminal of the doctor. When this terminal is equipped with an electronic card having a patient information processing software, the request information recorded in the electronic card can be used. Thus, the request information is recorded in the terminal of the doctor. This terminal of the doctor is equipped with a communication mechanism capable of communicating with the communication mechanism of the automatic processing system, so that it sends the request information together with a request message to accept processing to the sample container.

The terminal of the doctor may be in contact with the sample container. There can be some distance between them, within a limit that infrared rays can reach, and leakage is prevented by a shield from reaching sample containers other than the target one. The sample container, having received the request message to accept the processing, sends a receipt message to accept the processing and recites the request content.

If the request content and the recitation content are caused by a communication error to fail to coincide with each other, the request message to accept the processing and the receipt message to accept the processing are repeatedly exchanged to correct the error. There may be provided in a communication mechanism an adjusting mechanism for adjusting the infrared output, the detection sensitivity, the irradiation steric angle and the focal distance to adjust the communication mechanism automatically. If the communication error cannot be automatically corrected, so that the request content and the recitation content do not coincide with each other, or the receipt message to accept the processing is not replied, the terminal of the doctor sends a request message to interrupt the processing. The sample container replies the receipt message to interrupt the processing and interrupts the request. The terminal of the doctor displays the defect of the state of connection so that the connection error or the like would be resumed by an appropriate personnel. Moreover, if the communication defect is not eliminated even by repeating the communication, the terminal of the doctor sends a request message to cancel the processing to the sample container. This sample container replies a request message to cancel the processing to cancel the request. The terminal of the doctor reports the cancellation of the processing due to the communication defect and displays a message to the effect that the sample container should be replaced by another.

Here has been described a mechanism to evade the communication defect in the case that the terminal of the doctor sends to the sample container the request message to accept the processing. This communication defect evading mechanism can be applied to general communication between modules. The requesting module sends a request message and receives a reply of the receipt message containing the content recitation from the requested module. The processing continues normally if the two coincide with each other. If no coincidence is obtained even after messages are exchanged repeatedly, the request message to interrupt the processing and the receipt message to interrupt the processing are exchanged, and the alert message signifying the communication defect is sent to the terminal of the doctor to request the elimination of the communication defect. If the communication defect is not still eliminated, the request message to cancel the procedure and the receipt message to cancel the processing are exchanged, so that. the requesting module requests the terminal to replace the counterpart module. Thus, the cause for the communication defect, if any, can be eliminated, but this mechanism will not be referred to in the following description.

The abstract processing procedure is stored in advance for the anticipated individual kinds of sample and the individual anticipated items to be analyzed, in the non-volatile region of the memory mechanism of the sample container. At the stage that the request information arrives at the sample container, the abstract processing procedure corresponding to the sample kind and the requested items to be analyzed is selected by the information processor of the sample container. The abstract processing procedure for the requested items to be analyzed can be modified or extended from the terminal of the doctor.

For example, the terminal of the doctor sends a request message for offering the abstract processing procedure of the requested items to be analyzed to the sample container. The sample container replies the reply message for reporting the abstract processing procedure to the terminal of the doctor. If the replied abstract processing procedure has to be modified or changed, the request message for changing the abstract processing procedure, having a list of the preferred abstract processing procedure on the requested items to be analyzed, is sent. On the basis of this information, the sample container changes the abstract processing procedure and replies the changed abstract processing procedure as the reply message to the terminal. After the agreement has been reached between the terminal of the doctor and the sample container concerning the abstract processing procedure, the request message for executing the processing is sent from the terminal of the doctor to the sample container.

Here will be described the case that the analysis of urgency 3 (within a required deadline of 1 hour) on the biochemistry items to be analyzed (BUN,GOT,GPT and electrolytes Na, K and Cl) of the whole blood sample of a patient No. 3333 is required by a doctor No. 222 on Feb. 29, 1996, 9:20 A.M. The request information includes the sample container module, the sample specimen, the requested items to be analyzed and the abstract processing procedure. FIG. 9 schematically shows the request information to be stored in the memory of the sample container. The code CEN.ALQ.>.ANL of the abstract processing procedure representing the centrifuge, the aliquotation, the mission transfer and the analysis. This notation uses a part of the codes representing the high-level classification of the instrument.

In the present embodiment, the terminal of the doctor requests the sample container to offer the abstract processing procedure of the requested items to be analyzed, and the sample container replies a reply message for reporting the abstract processing procedure to the terminal of the doctor. The terminal of the doctor decides that the abstract processing procedure is sufficient, and sends the request message to execute the processing to the sample container instead of the request message to change the abstract processing procedure.

As a result, the sample container is stored with the purpose and procedure of the analysis as is shown in FIG. 9. In the analysis system, the sample specimen to be processed and the processing software are capsulated. In the field of information processing, the method of capsulating the algorithm describing the data to be processed and the processing method has been spotlighted in recent years as the object oriented programming. In the present system, the object to be processed and the processing method are capsulated, so that from this point of view the present system is understood as an object-oriented analysis system. This makes it easy to make the sample and the processing method to correspond to each other and to modify and reuse the software for the system and the module.

The sample container 15, containing the sample specimen and stored with the requested items to be analyzed (i.e., the purpose of processings by the system) and the abstract processing procedure, is placed in the accepting instrument 1 (as shown in FIG. 1). The sample container 15 executes the connection situation perceiving operation to establish a communication path with the accepting instrument 1 and comes into a connected state. Then, the connected state of the automatic processing system is perceived by use of, for instance, the extended adjacent communication mode to perceive the layout of the individual instruments connected to the system, and the individual identification information of the system. The accepting instrument 1 or the like is caused to perceive the situation of connection with the sample container 15 by the connection situation perceiving operation thereby to provide the information such as the individual identification information. As a result, the individual modules come into the state of connection with the system. Next, on the basis of the requested list of items to be analyzed and the abstract processing procedure, stored in the sample container 15, the individual instruments act in concert and cooperates with each other to execute the processings such as the delivery, the centrifuge, the aliquotation and the analysis, thereby accomplishing the purpose of the automatic processing system.

The cooperation and acting in concert between the modules are accomplished by repeating the operation that a certain module that stores the purpose and the corresponding procedure searches for an instrument module that is capable of processing the individual steps of the procedure and requests the instrument module to execute the processing. The sample container 15 is a module having the purpose in the form of the requested items to be analyzed, and is stored with the purpose and the procedure according to which it executes processings. The search for the functions of the modules are executed similar to the connected state perceiving operation by sending the request message to offer the function information and by receiving the reply message. Before requesting the target module having specific functions to execute the processing, the sample container has to reach the module, so the sample container sends a delivery requesting message to the other modules in between the target module and itself, and the modules in between deliver the container to the target module. Likewise, the sample container 15 sends a processing requesting message to the module having the processing functions, and the module executes processings.

The module such as the sample container 15 to be processed is stored with the purpose and procedure to execute the processing, is equipped with a mechanism for requesting the module that provides the processing function to offer the information of its function and to execute the processing. The module that provides the processing function is equipped with the mechanism for offering the information of its function in response to inquiry, and the mechanism for processing the sample on the basis of the request to execute the processing. Thanks to this arrangement, the cooperation and the concert between the modules can be realized by the simple means in a decentralized system configuration.

Here will be detailed the cooperative and concerted actions operations. The sample container 15 perceives that the abstract processing procedures (CEN.ALQ.>.ANL) for all the requested items to be analyzed are identical, and executes the operations on the basis of the processing procedure.

At first, the sample container 15 perceives that the first procedure is the centrifugation indicated by CEN, and searches for the centrifuging instrument. The CEN module is searched for by the extended adjacent communication. It is confirmed that the centrifuge instrument is participating as a module of the ID number 10 in the system and that the path to the centrifuge instrument 10 is 15.1.2.8.4.10. From this path information, it is perceived that the module is connected at present with the accepting instrument 1 of the ID number 1 so that it may be delivered in the direction to the module specified by the ID number 2, so that it may reach the centrifuge instrument 10.

The sample container 15 sends to the accepting instrument 1 a request message to offer the function information of the delivery, together with the path information (1.2.8.4.10) representing the delivery direction. The accepting instrument 1 examines whether or not the module is provided with the delivery function from the memory, and confirms that the module is provided with the function and is in the status of readily executing the function. The accepting instrument 1 then sends the reply message to report the function information representing the existence of the delivery function to the sample container 15. This sample container 15 sends the request message to execute the delivery processing to the accepting instrument 1 together with the path information (1, 2, 8, 4, 10), and this accepting instrument 1 delivers the sample container 15 to the two-way delivery instrument 2. At the stage that the sample container 15 leaves the accepting instrument 1 and reaches the two-way delivery instrument 2, a caution message of the connection situation change is issued in response to an interrupt signal from the sensor for detecting the connection situation change. In the accepting instrument 1, the two-way delivery instrument 2 and the sample container 15, the connection situation perceiving operation is executed again. When it is perceived that the sample container 15 is connected with the top of the two-way delivery instrument 2, the connection situation information is updated. Here will be omitted from now the description of the update of the connection situation information.

Secondly, the sample container 15 on the two-way delivery instrument 2 inquires the two-way delivery instrument 2 of the function to deliver in the direction to the CEN module similarly, and this two-way delivery instrument 2 replies that it has the function. The sample container 15 sends a request message to execute the processing of the delivery to the two-way delivery instrument 2, and this two-way delivery instrument 2 delivers the sample container 15 in the direction of the four-way delivery instrument 8.

Thirdly and fourthly, similar operations are repeated so that the sample container 15 is brought to the centrifuge instrument 10 through the four-way delivery instrument 8 and the two-way delivery instrument 4. The sample container 15 sends a request message to offer the centrifuging function information to the centrifuge instrument 10. The centrifuge instrument 10 examines the memory mechanism on whether or not it is equipped with the function, confirms that the function is present and ready, and replies that the module has the centrifuging function to the sample container 15 using the reporting message. The sample container 15 sends the request message to execute the processing of the centrifuging to the centrifuge instrument 10, and this centrifuge instrument 10 sends a message to the effect that the centrifuge instrument 10 accepts the request to execute the processing. The centrifuge instrument 10 centrifuges the whole blood sample, contained in the sample container 15, into blood serum and blood clot. The centrifuge instrument 10 informs the sample container 15 of the fact that the centrifugation is finished as a message of processing execution report.

Fifthly, the sample container 15 perceives that the next processing procedure is the aliquotation (ALQ), and searches for the aliquoting instrument. It is confirmed that the aliquoting instrument is participating in the system as the module having the ID number 11, The centrifuge instrument 10, which is the counterpart to the sample module at present, is inquired of the delivery function to the aliquoting instrument 11 and is requested to deliver the container 15 after the confirmation. The centrifuge instrument 10 delivers the sample container 15 to the aliquoting instrument 11.

Sixthly, the sample container 15, having reached the aliquoting instrument 11, inquires the aliquoting instrument 11 of the aliquoting function (ALQ), and requests the aliquotation, after the confirmation. In response to this request, the aliquoting instrument 11 aliquots the blood serum, for example, of the sample in the sample container 15 into a sample container 19 which is placed in advance in the aliquoting instrument 11. This aliquoting instrument 11 sends the report of the aliquoting processing to the sample container 15.

Seventhly, the sample container 15 perceives that the next processing is the mission transfer (>), and transfers the mission to the sample container 19. Specifically, the sample container 15 sends to the aliquoting instrument 11 the message to request the information necessary for the remaining processing (ANL) to be transferred to the sample container 19. The aliquoting instrument 11 returns a message to accept the mediation of the mission transfer to the sample container 15. The corrected information that the kind of the sample is the blood serum and that the form is an uncapped sample cup is added, and the message to request the mission transfer is sent to the sample container 19. This sample container 19 replies the message to accept the mission transfer to the aliquoting instrument 11. The sample container 19 stores the request information such as the ID number of the sample container module, the sample specimen, the requested items to be analyzed and the abstract processing procedure. FIG. 10 shows the requested information to be stored in the sample container 19. The message to report the result of the mission transfer is sent to the aliquoting instrument 11. In response to this, the aliquoting instrument 11 sends a message to report the result of the mediation of mission transfer to the sample container 15.

If the automatic processing system and the terminal of the doctor can communicate with each other as before, the sample container 15 sends to the terminal of the doctor a message to report that the aliquoting operation is complete, so that the mission is transferred to the sample container 19 having the ID number 19. This is a reply message to report the completion of the processing of the sample container 15 in response to the analysis requesting message from the terminal of the doctor. When this processing completion report is received by the terminal of the doctor, the sample container 15 once stops its operation.

The aliquoting instrument 11 sends a shunt requesting message to the sample container 15. In response to this message, the sample container 15 shunts, in other words, it moves away from the current location to that with less traffic. For example, one abstract processing procedure that realizes a shunt process, e.g., to be stored in a stocking instrument (STK), is fetched from the memory mechanism and set as the abstract processing procedure. The aliquoting instrument 11 sends the request message to offer the abstract processing procedure to the sample container 15 and receives the message to report the abstract processing procedure, i.e., the shunt process. This abstract processing procedure can be changed in response to a request message to change the abstract processing procedure. The aliquoting instrument 11 sends the request message to execute the shunt process to the sample container 15, and the sample container 15 searches for the stocking instrument (STK) in response to the request message. The sample container 15 finds out the stocking instrument 14 and requests each module to deliver the container 15 to the stocking instrument 14, and then sends the request message to execute the stocking processing to the stocking instrument 14. This stocking instrument 14 stocks the sample container 15. confirming this, the sample container 15 replies the stocking reporting message to the aliquoting instrument 11, and the shunting operation is complete.

Alternatively, the seventh step described above can be carried out in a slightly modified manner as follows:

The sample container 15 perceives that the next processing is the mission transfer (>), and transfers its mission to the sample container 19. Specifically, the sample container 15 sends to the sample container 19 a message to request the mission transfer together with the request information. In this case the mission is the remaining process, to analyze (ANL) the serum, and the other request information are those listed in FIG. 9. The sample container 19 inquires of the aliquoting instrument 11 about the status of the sample container 19. The aliquoting instrument 11 replies to the sample container 19 about the status of the sample container 19, i.e., its content is blood serum, its form is uncapped. The sample container 19 judges that it can take over the mission to analyze (ANL) the serum contained in itself, and replies with a message to accept the mission transfer to the sample container 15. Based on its intrinsic information, the request information received from the sample container 15, and the information received from the aliquoting instrument 11, the sample container 19 prepares new request information for itself, such as the sample specimen, the requested items to be analyzed, and the abstract processing procedure. FIG. 20 illustrates such request information. The sample container 19 stores this information into its memory.

The following operations of the sample container 15 is similar to that described above, i.e., to report the conclusion of its processing to the terminal of the doctors stop once, asked to shunt by the aliquoting instrument 11, carry out the shunting operation and gets stored in the stocking instrument 14.

In the above cases it is assumed that the mission borne by the sample container 15 is transferred entirely to the sample container 19, so that the responsibility to reply with the analytical results to the terminal of the doctor is equally transferred, as will be explained in the forthcoming paragraph. However, the system can also be designed so that the mission borne by the sample container 15 is preserved even after the mission transfer, and the sample container 15 acts as the requestor to the sample container 19. In this case, the sample container 15 acts just like the terminal of the doctor described above, i.e., it sends the request information together with a request message to accept processing to the sample container 19. Then the sample container 19 prepares new request information for itself. FIG. 21 shows such request information. Note that in this case the direct Requester is set to be the sample container 15 (CON15) instead of the terminal of the doctor (DR222). Hence the sample container 19 bears the responsibility to reply with the analytical results to the sample container 15. The other processes are similar to those described above (and those to be described in the forthcoming paragraphs), except that the sample container 15 does not cease to function even after the conclusion of its physical movements. Specifically sample container 15 must wait for the reply message from the sample container 19 that reports the analytical results. After receiving the reply message from the sample container 19, the sample container 15 sends a similar reply message, reporting the analytical results, to the terminal of the doctor.

If the automatic processing system and the terminal of the doctor can communicate with each other, the sample container 15 sends to the terminal of the doctor a message to report that the mission transfer has been carried out, and that the mission that had been borne by the sample container 15 has now been transferred to the sample container 19, that has the ID number 19. This serves as a reply message to report the conclusion of the processing of the sample container 15, in response to the message from the terminal of the doctor to request the analysis. After this processing conclusion report is accepted by the terminal of the doctor, the sample container 15 stops its operation.

Eighthly, the sample container 19 perceives that the next processing is the analysis (ANL), and searches the analysis instrument. As a result, the sample container 19 confirms that there are two analysis instruments 12 and 13. The path information to the individual modules of the analysis instruments 12 and 13 are 11.10.4.8.3.12 for the former and 11.5.9.6.13 for the latter. Hence, the number of modules (5,9,6) existing between the latter and the module 4 is 3, which is smaller than the number 4 of modules (10,4,8,3) existing between the former. Moreover, it is recognized that all the modules existing between the latter are the delivery instruments (DEL) so that the delivery can be executed at a high speed, and that the modules existing between the former include the centrifuge instrument 10 (CEN), so that the delivery cannot be executed at a high speed.

Hence, the sample container 19 judges that the analysis by the latter analysis instrument 13 is more efficient, and examines it as the first candidate. The analysis instrument 13 is inquired whether or not the individual items (e.g., BUN, GOT, GPT,Na,K,Cl) of the requested list of items to be analyzed can be measured. Having received the message reporting that all the items to be analyzed can be measured, the sample container 19 requests the individual delivery modules in the direction to the analysis instrument 13, by which effect, it reaches the analysis instrument 13.

Ninthly, the sample container 19 request the analysis instrument 13 with a request message to analyze the individual items (BUN,GOT,GPT,Na,K,Cl) of the requested list of items to be analyzed. In response to this request, the analysis instrument 13 analyzes the individual requested items of the blood serum sample stocked in the sample container 19. This result is sent as the process execution reporting message to the sample container 19. The sample container 19, having perceived that all the items are measured, stores the analysis result. If the automatic processing system and the terminal of the doctor can communicate with each other as before, the sample container 19 sends the analysis result together with the reply message to report the analysis completion to the terminal of the doctor. After this report has been accepted by the terminal of the doctor, the sample container 19 once stops its action.

The analysis instrument 13 sends a shunt request message to the sample container 19. In response to this request message, the sample container 19 shunts, like the sample container 15 explained in the latter half of the aforementioned seventh step.

Even if the sample container 19 cannot communicate with the terminal of the doctor at this time, it reports the analysis result including the processing executing report as soon as the communication path in between is established. The terminal of the doctor, if necessary, sends the request message to offer the process progress information to the sample container and receives the report message so that it can acquire the information on the progress situation of the delivering or analyzing processing and the analysis result.

In order to execute the analysis upon request of the terminal of the doctor, as described above, the sample container, according to the stored procedure, communicate with the instruments of the automatic processing system, to decide the best choice, to execute each procedure for the analysis and to report the analysis result to the terminal of the doctor. The present system is characterized in that it does not need any central processing instrument for controlling its entirety.

The operation of the system is initiated by the request information message from the terminal of the doctor to the sample container. However, the terminal of the doctor does not control all the modules of the present system, but gives merely simple and abstract message as the purpose. The terminal of the doctor need not be connected to the individual modules of the present system until it receives the report of the analysis result. As a result, the amount of the software upon the terminal of the doctor is so remarkably small that its operation can be remarkably easily verified, changed and extended.

In the present embodiment, moreover, the sample container does not control all the modules but exchanges the request/report messages with the individual modules, and leaves the detailed processing operations to the individual modules. In some cases, the request to execute the processing may be rejected by some modules, depending on the status of the modules. As described above, moreover, the first sample container 15 does not execute the processing operation to the last but may transfer the mission to execute the analyzing processing to another sample container 19. Upon the request from another instrument module, the sample container may execute a shunting operation, which is an example of the reversal of the power center. Thus, the present system can perform a flexible control by the decentralized manner, which is in significant contrast to the prior art.

The present embodiment which has been described as having one terminal for the doctor and one sample container. However, a plurality of such elements may be provided. In this modification, upon requests from the plurality of terminals of doctors, the plurality of sample containers execute the individual processing operations autonomously in parallel. Thus, the present system is characteristic of realizing an autonomous and parallel decentralized control mode.

The user of the present system gives a simple instruction to the sample container, and the detailed processing is left to the sample container. This sample container resembles an agent in the field of software. The present system is understood as an agent driven analytical system. The present system therefore, has an effect similar to the effect of making the system agent driven, i.e., easy development of the software and the ease of use of the system for controlling the system at a low cost.

In the present system, no limit is placed upon the arrangement and connection of the individual modules. The user can construct a system by determining the necessary arrangement of the modules and by connecting them. After the operation start has been instructed to start up the system by using the buttons of the control panel, the sample container, stored with the request information of the doctor, is placed in the accepting instrument. Even if the construction and arrangement of the individual modules are changed, the present system perceives the situation of connection automatically, so that the users need not consider the alteration in the control software to adjust to the change of construction and arrangement. Any desirable layout can be constructed according to the user's arbitrary determination of the arrangement of the system and by connecting the modules, thereby the plug-and-play is realized.

Since the users can construct an arbitrary system by combining the modules, the users can flexibly cope with the future system changes and replacements of broken modules, by keeping some spare modules at hand. As a result, multiple retainment of the modules (stocking of modules) tends to proceed. The manufacturer and the distributor can also offer the same module as a multi-purpose component to different users. As a result, the modules can be standardized and normalized. This urges the stocking of modules, and shortens the time period of delivery. Thanks to the module standardization and normalization, the design and the production can be facilitated to increase the production scale and to lower the price by the mass production effect and the stabilizing the production scale. These further promote the stocking effect to invite a satisfactory circle.

As has been described hereinbefore, the present system is an autonomous decentralized, can be easily constructed, corrected and extended, and can be changed in its arrangement while being operated. Moreover, the present system has a high resistance to troubles and can execute the most adequate processing exploiting the processing ability to the maximum. As has been clarified, the individual modules perform the cooperative and concerted operations to achieve the system operations efficiently. The aforementioned individual effects will be described in more detail in the following embodiments.

Second Embodiment

The first embodiment which has been described has neither any failure nor any trouble. In the automatic processing system of the present invention, when a specific module cannot function because of a failure, a trouble or an emergent situation, another module having an equivalent function acts as a proxy for that module. This mechanism will be described in connection with a second embodiment by using the arrangement of FIG. 1.

After the same operations as those of the first embodiment till the aforementioned eighth step have been carried out, the analysis instrument 13, one of the two analysis instruments that are found out by the search of the sample container 19, is examined as a first candidate in the course of the eighth step. For example, the sample container 19 sends a request message to offer the function information to the analysis instrument 13, and receives a report that the item (BUN) cannot be measured because of a too small amount of the remainder of the reagent. In order to examine the analysis instrument 12, the sample container 19 sends to the analysis instrument 12 the request message to offer the function information on whether or not the individual items (BUN, GOT,GPT,Na,K,Cl) of the requested list of items to be analyzed can be measured. The sample container 19 receives the report that all the items can be measured, determines the delivery to the analysis instrument 12 and requests the individual modules for the delivery in the direction to the analysis instrument 12.

The operations at and after the ninth step are similar to those of the first embodiment excepting that the analysis instrument 12 having the ID number 12 acts as the proxy for the analysis instrument 13 having the ID number 13.

Even if a specific module does not function as in the present embodiment, it is automatically avoided, and a module having the same function can act as the proxy to achieve the same processing operations so that a high resistance to failures can be achieved. The present embodiment which has been described has a plurality of analysis instruments, but the delivery routes also may be in plurality.

Figure 11:
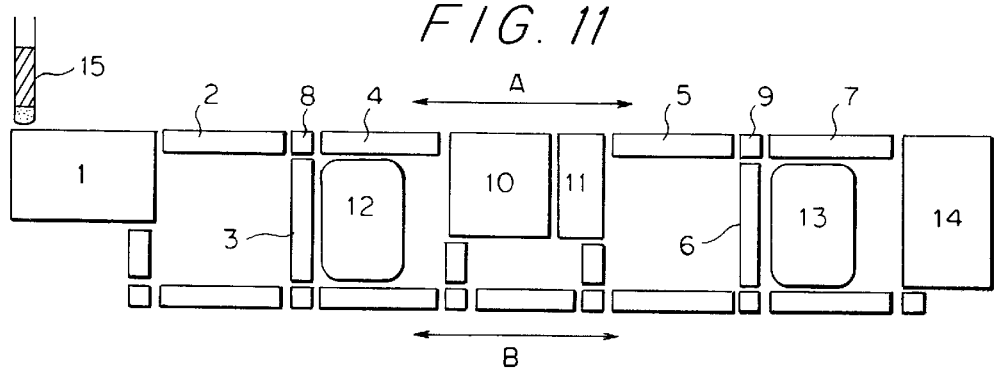
FIG. 11 is a schematic arrangement diagram of an automatic processing system having a plurality of delivery routes of a second embodiment.

FIG. 11 illustrates an abstract arrangement diagram showing an automatic processing system having a plurality of delivery routes according to a second embodiment of the present invention. In FIG. 11, squares having no reference numeral are four-way delivery instruments, and rectangles are two-way delivery instruments. The delivery efficiency is improved by providing a delivery route A and a delivery route B. Even if either of the delivery routes fail, the delivery function is maintained by searching, determining and selecting the correctly functioning delivery route by the sample container. The faulty delivery route is automatically bypassed.

According to the present embodiment, the faulty module can be automatically avoided to provide a high resistance to failures.

Third Embodiment

In the present embodiment, the partial replacement and extension of the system during operation will be described. From the arrangement of FIG. 1, the two-way delivery instrument 4 is taken out without halting the entire system so that it may be subjected to a periodic maintenance, for example.

Figure 12:
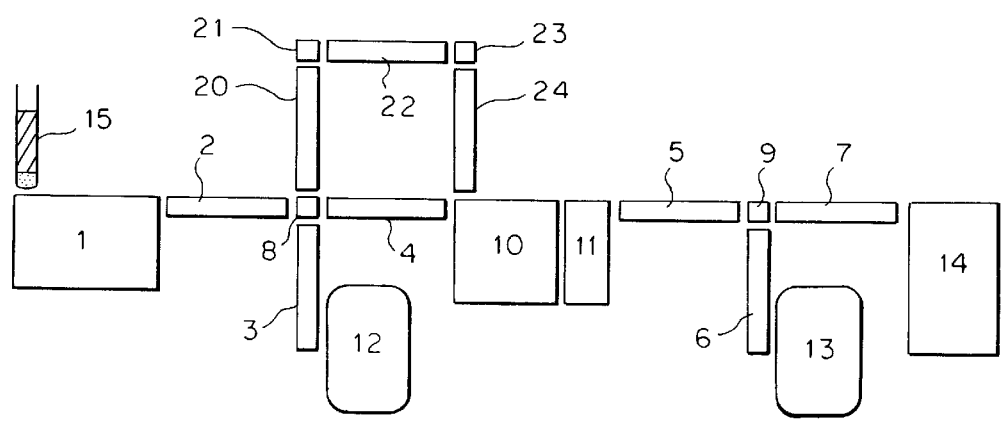
FIG. 12 is a schematic arrangement diagram at the end of a first step for explaining a third embodiment.

Firstly, modules 20, 21, 22, 23 and 24 are connected, as shown in FIG. 12, while operating the entire system. After these modules have been powered on, the operation start is instructed by using the buttons of the control panel on the newly added modules. The added modules execute the aforementioned connection situation perceiving operation as one step of the start-up procedure at the start of the operation to perceive the arrangement of the system. The existing individual modules execute again the connection situation perceiving operation to perceive the situations of connection of the newly added modules. As a result, these new modules join the automatic processing system so that the automatic processing system begins to function according to the new arrangement of FIG. 12.

As routes from the left side of the module 8 to the right side of the module 10, there are established not only the original route (8.4.10) but also the second route (8.20.21.22.23.24.10). When the sample container 15 is to be delivered from the left side of the module 8 to the right side of the module 10, which route is to be adopted is judged by the information processor 16 of the sample container 15, as follows. First of all, the amount of traffic on the two routes and the estimated time for the delivery are acquired by inquiring of the function information of the modules corresponding to the individual routes. From these pieces of information and the deadline recorded in the memory 17 of the sample container 15, it is judged which route the sample container 15 should adopt.

Secondly, a temporary halt is instructed to the two-way delivery instrument 4 by using the buttons of the control panel on the instrument. The two-way delivery instrument 4 comes into a temporary halt preparing mode to deliver only the sample container thereon and the sample containers having already been accepted the request to execute the delivering process. Afterwards, even if a request to offer the delivering function information has newly arrived from the other sample containers, the function information incapable of accepting the delivery, because of the temporary halt preparing mode, is sent as a reply. Even if the processing executing request has newly arrived, the reject message is replied because of the temporary halt preparing mode. From now on, the sample containers will select the delivery through the second route (8.20.21.22. 23.24.10).

Figure 13:
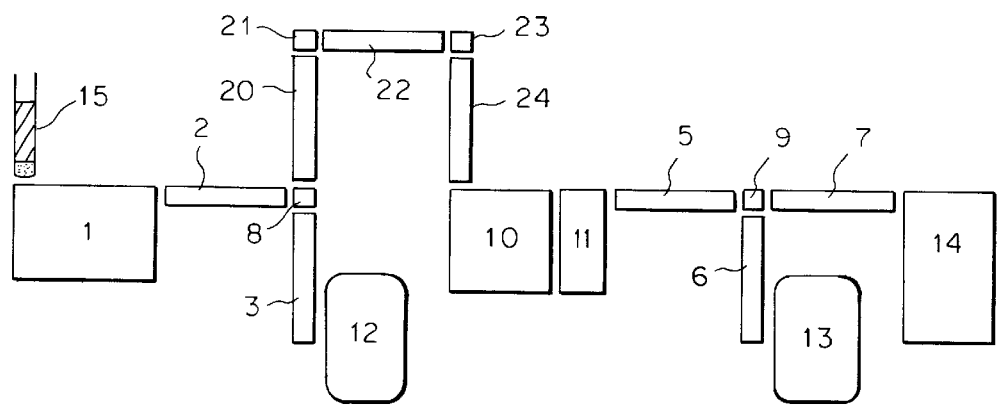
FIG. 13 is a schematic arrangement diagram at the end of a second step of the third embodiment.

The two-way delivery instrument 4 comes into a temporary halt mode when the delivery of the sample containers, having already been promised to execute the delivering processing, is wholly completed. The achievement of this temporary halt is indicated by the lamp on the control panel. In this temporary halt state, the two-way delivery instrument 4 is taken out from the system. The modules 8 and 10 detect the change in the situation of connection and execute the connection situation perceiving operation again to perceive the removal of the module 4. FIG. 13 shows the abstract arrangement diagram at the end of the second step.

Figure 14:
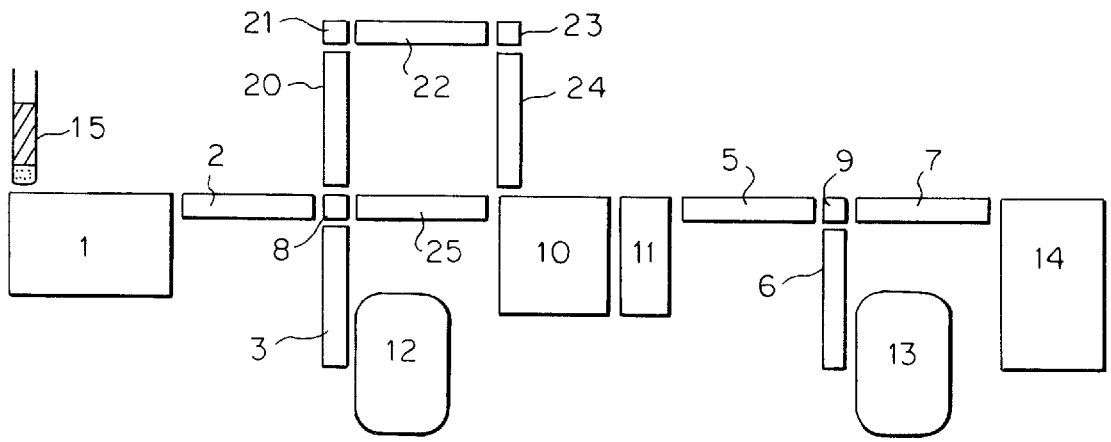
FIG. 14 is a schematic arrangement diagram at the end of a third step of the third embodiment.

Thirdly, as a result of the periodic maintenance of the two-way delivery instrument 4, consumable parts will have to be replaced, so that the two-way delivery instrument 25 having an identical function is connected in the position, at which the two-way delivery instrument 4 had been connected, in the similar procedure as that for the module addition of the foregoing first step 1. FIG. 14 shows an abstract arrangement diagram at the end of the third step.

Fourthly, in a procedure similar to that of the module removal at the foregoing second step, the modules 20, 21, 22, 23 and 24 are removed, to provide an arrangement in which the module 4 is replaced by a module 25.

At any stage of the aforementioned individual steps, the operation of the other modules are not stopped, so that the entire system continues to operate. In the present embodiment, the two-way delivery instrument 4 can be removed and replaced selectively while the operation of the entire system is maintained continuously.

For the present embodiment, addition, removal and replacement of the delivery instruments have been described, but other modules can likewise be added, removed and replaced. Although the correctly functioning normal module was replaced in the above explanation, the abnormally halted modules can likewise be removed and replaced to replace the faulty modules without halting the entire system, thereby to improve the resistance to failures.

According to the present embodiment, the modules can be partially added, replaced and extended while continuing the operation of the system. In this case, the sample container operates while confirming the function information of the individual modules, and the modules to be halted, will not be halted before they finish the operating process already undertaken, by establishing a transfer period, i.e., the temporary halt preparing mode. By devising the bypass as shown in the present embodiment, therefore, the system can be rearranged without any entire halt even in the case of replacement or removal of its components. This rearrangement is effective in the automatic processing system which is required to consecutively execute a highly emergent analysis, such as in the case of a clinical diagnosis. In the absence of the central processing instrument for controlling the entirety, moreover, it is unnecessary to consider the updating of the software. As a result, the system can be extended in a short time period, with a saved labor and at a low cost. For example, the operator can change the instrument arrangement freely.

Fourth Embodiment

In the present embodiment, the emergent recovery from failures by using the manual operations together will be described in connection with the arrangement of FIG. 1. The operations are identical up to those of the seventh step of the first embodiment. At the eighth step, the sample container 19 requests the aliquoting instrument 11 to execute the delivering processing in the direction to the analysis instrument 13e but the delivery cannot be executed because of the failure of the aliquoting instrument 11. This aliquoting instrument 11 reports the fact that it has lost the delivery function and its cause together, in the reject message, to reject the execution of the delivering processing.

Ninthly, the sample container 19 perceives that it cannot move anywhere because it is on the malfunctioning instrument 11, and sends the caution message of the failure of the delivering process function to request the terminal of the clinical laboratorian to improve the situation and a similar caution message to the terminal of the doctor to report that the analysis result can not probably be sent in time for the deadline.

Tenthly, the clinical laboratorian manually brings the aliquoting instrument 11 into the manual operation mode. The laboratorian transfers the aliquoted sample container 19 from the aliquoting instrument 11 to the two-way delivery instrument 5 and repairs the aliquoting instrument 11.

Eleventhly, the sample container 19 and the two-way delivery instrument 5 perceive that they are newly connected with each other, and execute the connection situation perceiving operation to perceive the situation of connection. The sample container 19 confirms that the abstract processing procedure in the memory mechanism is for the analyzing operation (ANL). From now on, the procedure of the search of the analysis instrument, the candidate selection, the function confirmation and the delivery request are executed, as at and after the eighth step of the foregoing first embodiment, and the analyzing operation is completed after the delivery to the analysis instrument 13.

Incidentally, at the instant when it is confirmed, after the transfer from the faulty aliquoting instrument 11 to the two-way delivery instrument 5, that the delivery route has been reestablished, a cancel message to cancel the cause message is sent to the terminal of the clinical laboratorian and the terminal of the doctor. Upon the request for the delivery from other sample containers, the reply message to report that the delivery is impossible is sent to the aliquoting instrument 11 in response to the request to offer the delivering function information, if the aliquoting instrument 11 is not yet repaired or if the manual operation mode is not canceled. Until then, it is judged that the delivery through the aliquoting instrument 11 is impossible.

In the present embodiment, each module can reconfirm the situation of connection at any time, and the sample container is stored with the purpose and procedure of the processing operation. As a result, even if the delivery instrument fails, this failure can be recovered merely by transferring the sample container from the faulty module to the correctly functioning module, to provide a system having a high resistance to failures. Even in the case of a disconnection of the delivery route between the instruments because of the shortage of the delivery instruments, the transfer can be manually executed. Even if the delivery instrument is not present at all, the analysis can be executed by the manual delivery between the centrifuge, aliquoting and analysis instruments. Although the manual recovery of failures has been described above, priority processings of the emergent specimen and re-inspection can be similarly executed by using the manual operations together.

From the standpoint of preventing the deadlock often encountered in a decentralized system caused by the loss of purposes or by mutual concessions, the mechanism of cooperation and acting in concert between the modules of the foregoing embodiments for realizing the complicated procedure necessary for the processing operation have been described.

In the automatic processing system, a number of samples are consecutively processed. Here will be described the mechanism for preventing, by cooperation and concert, the deadlock caused by the competition of a plurality of sample containers for an instrument resource. The contemplated execution, or the second characteristic for achieving the cooperative and concerted operation of the present automatic processing system, will be described in connection with fifth to eighth embodiments.

Fifth Embodiment

The automatic processing system of the present embodiment is arranged by combining the modules having mechanisms basically similar to those of the foregoing individual embodiments. A first difference resides in that a plurality of sample containers are provided.

In the foregoing embodiments, the function information is investigated only immediately before the request to execute the process. A second difference resides in that at the time of the operation of each sample container, the process is executed by investigating the operations of several later steps in advance, by making a plan and by making a reservation with a module which is scheduled to be requested to execute the processing (in the future).

A third difference resides in that each processing instrument accepts not only a request from the sample container in direct contact with its module but also a request to reserve from another remote sample container, and makes a processing schedule to inform the sample container of the schedule, so that it processes according to the schedule, if acknowledged by the sample containers. By this scheduled executing operation, the optimization on the basis of the estimation and the formation of order are achieved, thereby extending the perspective further not only in distance but also in time.

The specific description will be made on the situations at and after the eighth step of the second embodiment, for example. In the arrangement of FIG. 1, the sample container 19 is located over the aliquoting instrument 11 to search the analysis instrument and confirm the function. As a result, the analysis instrument 13 cannot measure and request the transfer in the direction to the analysis instrument 12. Here will be described an example, in which another sample container 26 having requested to analyze the same item is placed over the accepting instrument 1.

First of all, here will be described a problem arising when there is adopted the same operating method as that of the foregoing second embodiment. In this case, the sample container 19 sends to the aliquoting instrument 11 a request message to offer the function information of the delivery in the direction to the analysis instrument 12, and requests the delivery when it receives a report that the aliquoting instrument 11 has the delivery function. The sample container 19 is delivered through the centrifuge instrument 10 to the two-way delivery instrument 4. The sample container 26 requests the four-way delivery instrument 8 for the delivery to the two-way delivery instrument 4.

If the delivery route of the two-way delivery instrument 4 or the four-way delivery instrument 8 is a double track line, bidirectional delivery can be simultaneously executed by a single module. Alternatively, if a shunting place is prepared in the module, one can be passed while the other is being shunted. If both delivery routes have a single track line, that is, if the delivery can be executed not simultaneously but only in one way and has no shunting place, the system will be in a deadlock state.

Since the sample container 26 is on the four-way delivery instrument 8, the sample container 19 can not be delivered to the four-way delivery instrument 8 by the two-way delivery instrument 4. Contrarily, the sample container 19 is on the two-way delivery instrument 4, so that the sample container 26 can not be delivered to the two-way delivery instrument 4 by the four-way delivery instrument 8. This deadlock state can be simply solved by interposing a negotiating mechanism between the sample container 19 and the sample container 26, so that one shunts in a predetermined place to first allow the other to pass, and then allow itself to go. Despite of this solution, however, the deadlock, in which the plurality of sample containers compete for an instrument, can be prevented in advance in the following manner.

In the present embodiment, the sample container 19 and the sample container 26 inquires in advance of the functions and the future plan of the individual delivery modules corresponding to the delivery routes and make reservations of delivery with the plurality of delivery modules. In response to the requests of delivery from the plurality of sample containers, the delivery instruments communicate with each other to adjust the plan so that the deadlock state may not arise. As a result, the contemplated operations, based on a long termed and wide ranged view point, can be executed to prevent the trouble such as the deadlock, in advance.

First of all, the sample container 19 requests the individual modules 11, 10, 4, 8, 3 and 12 corresponding to the routes to the destination to deliver itself in the following procedure. The individual modules are requested to offer the function information of the delivery, and it is perceived from the report that the delivery is possible and that all the delivery routes are single track lines. Next, the request message to reserve the delivering processing is sent to request the reservation. Since, at this time, all the delivery routes are single track lines, the consecutive delivering processing is required in this section, and it is additionally described that an exclusive and continuous reservation is necessary. The sample container 26 likewise requests the individual modules 1, 2, 8, 4 and 10 corresponding to the routes to the destination to deliver itself along the routes.

In response to a predetermined amount of request messages to reserve the individual modules on the delivery routes, the acknowledgement message is sent as a reply. Next, the modules are so re-arranged on the time axis that there are no overlappings, and the processing plan is made in the following procedure. This procedure will be described with reference to FIG. 15. Considering the desire of the sample container 19 of the prior request, the modules make their own successive delivery schedules up to the module 12 such that the module 11 delivers thereon in the leftward direction of FIG. 1 from time 0 to time T1, next the module 10 from time T1 to time T2, and the module 4 from time T2 to time T3 and so on. At this time, there are inquired and considered the time schedule of the preceding module and the reservation situation of the scheduled destination of the delivery. Next, for the sample container 26, requesting the reservation later, the rightward delivery schedule is made in the order, from the module 1 at time 0.

Figure 15:
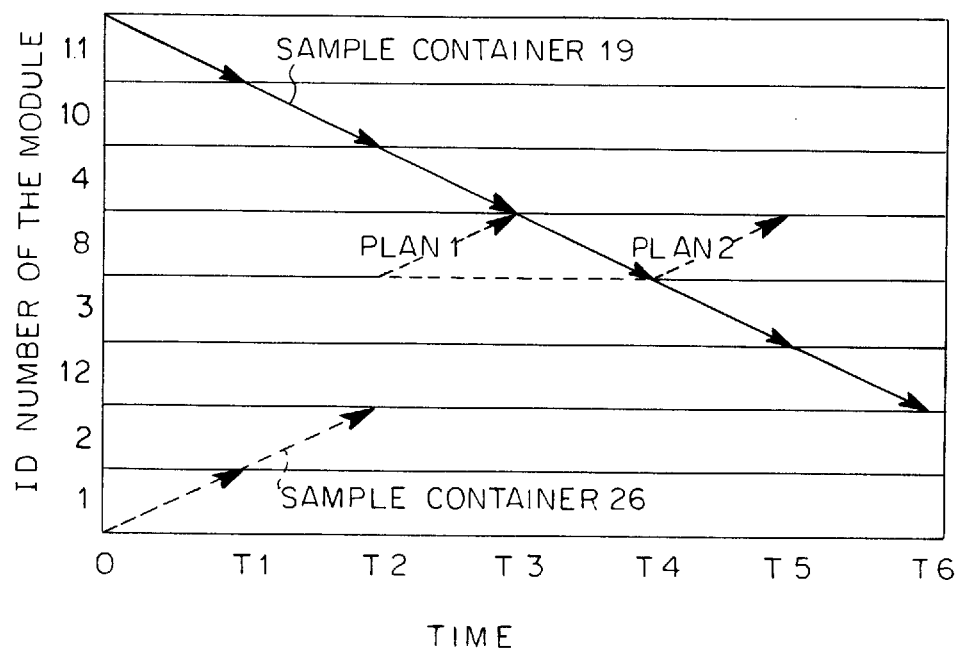
FIG. 15 is a diagram schematically showing the intermediate point of making a delivery schedule plan of a contemplated execution of a fifth embodiment.

This intermediate situation is shown in FIG. 15. The abscissa indicates the time; the ordinate indicates the kind of module; arrows of solid line indicate the delivery schedule of the sample container 19; and arrows of dotted line indicate the delivery schedule of the sample container 26. For simplicity, it is assumed that the time taken to go across each instrument be constant. According to the plan 1, the sample container 19 is delivered from the right to the left over the module 4, and the sample container 26 is delivered from the left to the right over the module 8. According to this plan, however, the deadlock occurs between the modules 4 and 8. The module 8! therefore, discards the plan 1 and adopts a plan 2, in which the sample container 26 is not delivered but stocked in the module before the sample container 19 passes, and the delivery of the sample container 26 is started at time T4 when the sample container 19 passes by.

Thus, the modules are inquired of whether or not there is a plan for reversely delivering another sample container B, before placing a sample container A into the single track section where no shunt place is provided, during the time period from this placement to the time point when the sample container A passes. When reverse delivery is scheduled, the delivery of the sample container A is postponed till the passage of the sample container B so that crossing in the diagram can be prevented, preventing the deadlock in advance.

After this, the delivery plan of the sample container 26 is likewise prepared for the modules 4 and 10. At the stage where these plans are prepared, each module sends the message to report the processing reservation to each sample container thereby to present the plan. Each sample container judges the presented plan and sends a request message to change the processing reservation, if necessary, to negotiate till a consent is achieved. After the request message to fix the processing reservation has been sent after the consent, the requests to execute the processing are sequentially made as in the foregoing individual embodiments, and the processing progresses according to this plan. If the plan has to be changed in an emergency, the request message to change the processing reservation is sent to all the related modules, and the plan is remade.

The present embodiment has been described on the case that the sample container cannot be measured in one analysis instrument so that it has to be delivered to another analysis instrument, namely, reversely delivered along the delivery route. The contemplated execution of the present invention is also effective for other cases. These cases are exemplified by the case in which the reverse delivery is required for the re-analysis, the case in which the replacement of the sensor or reagent is required so that the analysis instrument is anticipated to be temporarily halted in its analyzing operation and bypassed to another analysis instrument, or the case in which a caution has to be made beforehand because the time when it is expected that the processing will be complete, predicted from the time necessary for each processing, is later than the deadline.

As has been described in connection with the present embodiment, the optimization and formation of order can be achieved on the basis of prediction by searching for the operation of not only the closest module but also a remote module in advance to make the plan, and by executing the processing actually after the reservation. By the contemplated execution of the present invention, the optimization and formation of order can be achieved to realize the cooperative operation between the modules autonomously operating for their independent purposes.

Sixth Embodiment

In the present embodiment, the contemplated execution operations are performed as in the fifth embodiment, and the priority is introduced and weighted for evaluation, so that the efficiency of the function of the entire system may be raised.

The present embodiment is different from the fifth embodiment in the operations at and after the time the individual sample containers accept the function information from the individual instruments. The time period taken to execute the processing is also accepted as the function information and considered to make a plan. Each sample container sends to each instrument a request message to reserve the processing including the information of the priority of each sample container. The instrument makes an execution plan by adjusting the requests from the plurality of sample containers while considering the priority.

The information of the priority is the code information representing the kind of analysis (an emergent analysis or an ordinary analysis) and can use the "urgency" out of the information which the sample container is requested to offer by the terminal of the doctor, for example. Moreover, the desired time at which the processing ends is used as the "deadline" information.

In the system arrangement of FIG. 1, it is assumed the sample container 19 is on the aliquoting instrument 11 at 9:38 on Feb. 29, 1996 and decides to be delivered in the direction to the analysis instrument 12, so that the sample container 26 is placed on the accepting instrument 1. The operations on and after this instant will be described in the following.

It is also assumed that the urgency and deadline of the sample container 19 are "3" and "10:20, Feb. 29, 1996", respectively, and that the urgency and deadline of the sample container 26 are "4 (within a deadline of 30 minutes)" and "9:50, Feb. 29, 1996", respectively.

Each sample container refers to the list of the abstract processing procedure in its memory mechanism at the time when it participates in the automatic processing system, and inquires the instrument, which has a function for the individual processings necessary for the end of the final processing, of the function information to determine the route After this, the sample container makes a reservation in the individual processing instruments corresponding to the route. At this time, the function information includes the information of validation/invalidation of the function and the estimated time taken to execute the processing of the individual functions.

The sample container 19 receives the estimated time taken to execute the processing from the individual modules (11, 10, 4, 8, 3, 12) corresponding to the delivery route to the analysis instrument 12. For simplicity, the estimated value of this time is set at one minute. The request message to reserve the delivering/analyzing processing of the urgency 3 has already been sent. The reservation including the element of the time taken to execute the processing, as shown by the solid line in FIG. 16, has already been received, and is scheduled to provide the final result at 9:44. This is before the deadline (10:20, Feb. 29, 1996) in its own memory mechanism and satisfies the demand of the doctor.

It is assumed in the present embodiment that the centrifuge instrument 10 has a shunting place to allow the two sample containers to cross.

If the sample container 26 is placed on the accepting instrument 1, it executes the connection situation perceiving operation, participates in the automatic processing system, refers to the list of the abstract processing procedure in its own memory mechanism and determines the route by inquiring, of the function information, the instrument which has a function to execute the individual processings necessary for ending the final processing. The function information includes the estimated time taken to execute the processing the individual functions. The sample container 26 confirms that the objective analysis can be executed, by following the route, i.e,. 1, 2, 8, 4, 10 and 11 (for the aliquotation), 11 (thereafter, the delivery by another sample container), 10, 4, 8, 3 and 12. Here is assumed that the processing including the deliveries of the individual instruments for which it takes individually one minute.

The processing time periods are summed and added to the present time 9:38, Feb. 29, 1996, then the result is 9:50, Feb. 29, 1996. With no waiting time, the final result can be obtained by the deadline (9:50, Feb. 29, 1996) in the own memory mechanism.

Next, the sample container 26 asks the individual processing instruments on the route for reservations of the delivering and analyzing processings. The information of a high priority (the urgency 4) is set together with the request message to reserve the processing. In response to this request to reserve the processing, the instrument makes an execution plan while considering that priority. Because of no appointment, the modules 1 and 2 incorporate the reservation of the sample container 26 into their own processing plans. When the sample container 26 is reserved, the module 8 predicts the cross of the diagram and the occurrence of the deadlock and judges which desire can be granted preferentially to achieve the highest efficiency as a whole, by building up hypotheses for two cases.

Figure 16:
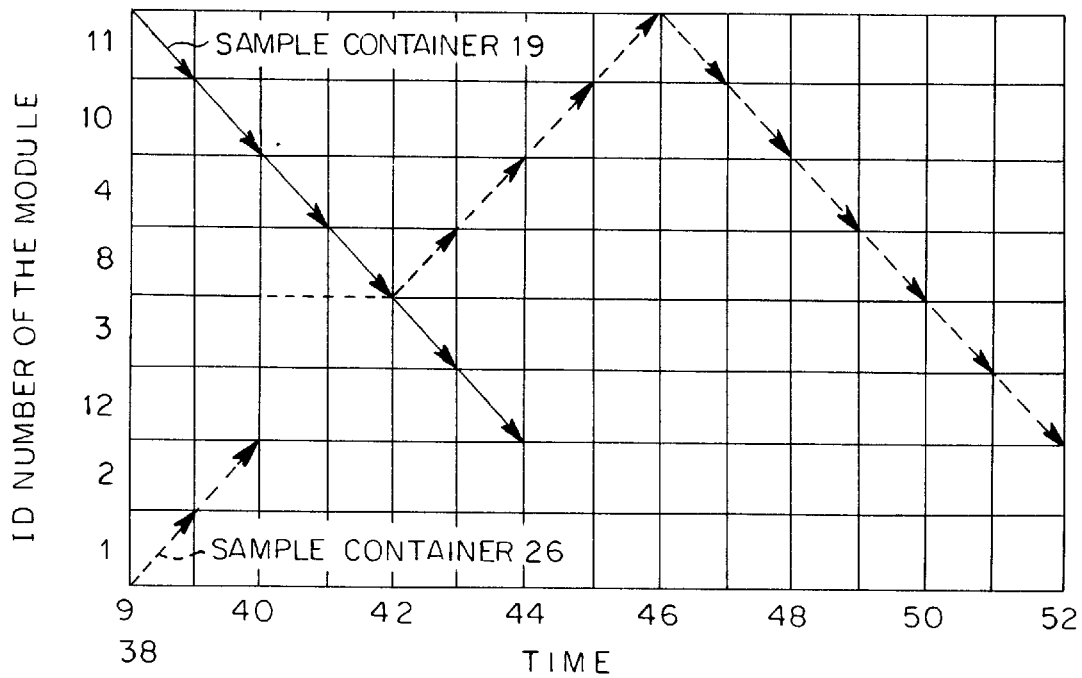
FIG. 16 is a diagram of the case in which the sample container 19 of a sixth embodiment is preferentially processed.
Figure 17:
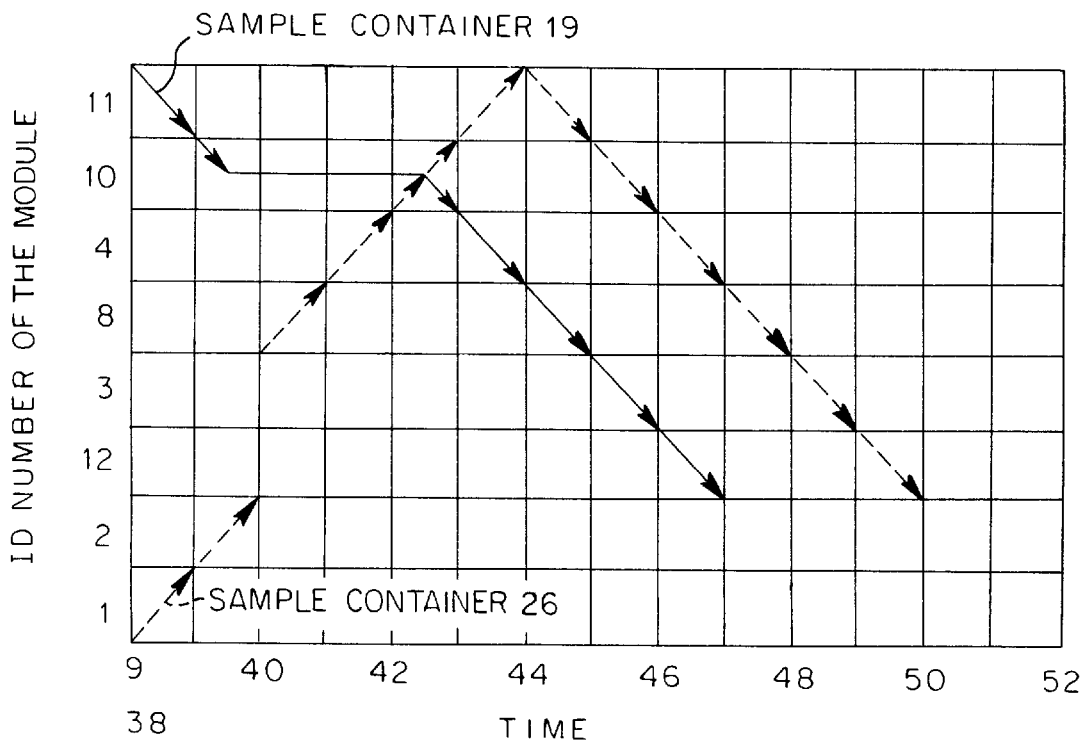
FIG. 17 is a diagram of the case in which the sample container 26 of a sixth embodiment is preferentially processed.

FIGS. 16 and 17 are diagrams of the individual cases in which the sample container 19 and the sample container 26 are processed preferentially. According to the first hypothesis of FIG. 16, the plan of the sample container 19 retaining the reservation in advance is ensured so that the reservation of the sample container 26 may be kept away from the deadlock. The module 8 once stores the first hypothesis in its own memory mechanism. The module 8 does not allow the sample container 26 to pass till the end of the delivery of the sample container 19, so that no deadlock is caused.

Next, the module 8 builds up the second hypothesis of FIG. 17. The module 8 sends to the sample container 19 the reply message to reject the processing reservation till the reservation end of the sample container 26. The sample container 19 sends the request message to cancel the processing reservation to all the modules on the route to cancel its own reservation temporarily and stands by till the end of the reservation of the sample container 26. In response to the subsequent request of the module 8, the sample container 26 retains the subsequent reservation of the module 8, as shown by dotted lines in FIG. 17, to report the reservation acquisition result to the module 8. Next, in response to the request of the module 8, the sample container 19 makes a reservation on the route. The sample container 19 makes the reservation of the modules 11 and 10 successively, but the module 10 perceives that the deadlock occurs at the modules 4 and 8. Making a plan that the sample container 19 is held in the shunting place of the module 10 from the time 39.5 minutes to the time 42.5 minutes at which the sample container 26 to pass, therefore, this reservation is retained for the sample container 19. The intersection of the sample containers 19 and 26 in the shunting place in the centrifuge instrument 10 is expressed as the cross of the diagram at 9:42.5.

The sample container 19 reports the reservation acquisition result to the module 8, and this module 8 stores the second hypothesis in its own memory mechanism. In the case of the first hypothesis (hereinafter referred to as the plan 2), the analysis of the sample container 19 is ended at 44 minutes, and the analysis of the sample container 26 is ended at 52 minutes. In the case of the second hypothesis (hereinafter referred to as the plan 3), the analysis of the sample container 19 is ended at 47 minutes, and the analysis of the sample container 26 is ended at 50 minutes.

Which plan is adopted by the module 8 is determined by various manners. The simplest method is to merely adopt preferentially the plan having a higher urgency. Because of simplicity, this method is effective to judge a simple problem which container of the plurality of sample containers is to be delivered earlier in the same direction. If this method is applied to the present embodiment, the plan 3 is adopted by delivering preferentially the sample container 26 of the urgency 4, not the sample container 19 of the urgency 3. For the present embodiment, the case in which one sample container is delivered in each direction is considered. If, however, the number of sample containers relating to the reverse delivery concerned with the hypothesis, the number of sample containers is multiplied by the urgency and the resultant value is weighted so as to evaluate the effect.

If the deadline is known and the time period for the processing can be anticipated, according to the second judging method, it is investigated whether or not the processings of the individual sample containers are completed before the deadline, and the sample container fulfilling the deadline is processed preferentially. In the present embodiment, the plan 2 fulfills the deadline (10:20) of the sample container 19 but not the deadline (9:50) of the sample container 26. on the other hand, the plan 3 fulfills both the deadline (10:20) of the sample container 19 and the deadline (9:50) of the sample container 26. Therefore, the second judging method adopts the plan 3. In this example, it is possible to apply the clear criteria for judging whether or not the deadline is fulfilled.

On the other hand, the third judging method can be adopted if either plan can fulfill the deadline or oppositely if neither plan can satisfy. For example, a synthetic judgment can be made based on the value of the comparison between the required time from the time of request to the time of result and the demanded deadline, weighted with the urgency. In the aforementioned examples, the required time of the sample containers 19 and 26 are respectively 22 minutes and 32 minutes for the plan 2 and 27 minutes and 30 minutes for the plan 3. These are compared with the time periods (60 minutes and 30 minutes) demanded by the doctor for the individual sample containers, and an evaluation function of y=(the demanded time/the time actually taken) is employed. Then, the y values of the sample containers 19 and 26 are respectively 2.22 and 0.94 in the case of the plan 2 and 2.22 and 1 in the case of the plan 3. Simply, these y values can be summed for the individual sample containers to evaluate the individual plans. These sums are respectively 3.16 and 3.22 for the plans 2 and 3, so that the plan 3 having a larger evaluation value is adopted. Moreover, the y values before summed can be weighted by multiplying them by the urgencies (3 and 4 for the sample containers 19 and 26, respectively). The evaluation values of the individual plans of this case are 10.42 and 10.66, so that the plan 3 is also adopted. If the number of sample containers is 2 or more, these y values can naturally be incorporated into the sums. To fulfill the deadline, moreover, another evaluation function where further weighing is applied can be adopted. The module 8 thus having decided to adopt one of the two plans informs the module of the execution plan based on the adopted plan.

In the present embodiment thus far described, the priority is introduced and weighted for the evaluation so that the plurality of sample containers can be harmonized to enhance efficiency and optimize the system operations.

Seventh Embodiment

In the present embodiment, in order to realize the cooperative operations of the individual modules, the reliability of a module is evaluated by another module so that the latter module changes the handling of the former on the basis of the evaluation result. For example, an index of a reliability parameter is introduced and is stored in the modules adjacent to each module. This will be specifically described in connection with the example of FIG. 1. The two-way delivery instrument 3 stores the reliability parameter of the analysis instrument 12 and the reliability parameter of the four-way delivery instrument 8.

The reliability parameter is initialized to an initial value "ordinary" as one step of the adjacent situation perceiving operation when each module participates in the automatic processing system. Here it is assumed that the analysis instrument 12 does not function as expected, due to the shortage of a reagent, making the analysis impossible. The two-way delivery instrument 3 changes the reliability parameter of the analysis instrument 12 in the memory mechanism into "rather low". If the analysis instrument 12 operates, as scheduled, for a predetermined time period, the evaluation parameter is sequentially raised to "ordinary", "rather high", "high" and "extremely high". If unstable operations such as failures are subsequently repeated, on the contrary, the evaluation parameter is sequentially lowered to "low" and "extremely low".

When the sample container 15 inquires the analysis instrument 12 of the analytical function information or makes a reservation, it also requests the adjacent two-way delivery instrument 3 to offer the reliability parameter information of the analysis instrument 12. The sample container 15 considers the reliability parameter when it makes its own schedule. If the parameter is "extremely high", for example, the sample container 15 relies upon and entrusts the analysis instrument for the analysis. If "extremely low", on the contrary, the sample container 15 adopts another plan to ask another analysis instrument having a higher reliability, even if it is at a little more distance, for the analysis, thereby to lower the risk. By thus ranking the processing instruments according to the operation results on the basis of the operation results to optimize the operating method, it is possible to operate the system highly reliably while avoiding a poorly reliable module which may be a weak point of the system.

Eighth Embodiment

In the present embodiment, as in the foregoing seventh embodiment, in order to realize the cooperative operations of the individual modules, the reliability evaluation of a module is made by another module so that the handling of the former module by the latter is changed on the basis of the evaluation result. However, a difference resides in that the module to be evaluated is the sample container. The reliability parameter is introduced concerning the sample container 15, for example.

Specific description will be made in connection with the example of FIG. 1. When the sample container 15 is placed on the accepting instrument 1, this accepting instrument 1 stores the initial value "ordinary" of the reliability parameter of the sample container 15. Simultaneously as the sample container 15 is delivered to the two-way delivery instrument 2, the accepting instrument 1 sends the reliability parameter of the sample container 15 to the two-way delivery instrument 2, so that this delivery instrument 2 stores the value of the reliability parameter. The values are also stored in succeeding instruments.

If the sample container 15 fails and exhibits behaviors such as to cease to operate as a module, to repeat sending an unreasonable request to the processing instruments, or to stray meaninglessly over the delivery instruments, for example, in the order of the modules 2, 8, 4, 8, 2, 8 and 4, the module for delivering the sample container 15 evaluates the reliability parameter of the sample container 15 in its own memory mechanism as "rather low". If the sample container normally functions for a predetermined period, the evaluation parameter is sequentially raised to "ordinary" and "rather high". If the sample container subsequently repeats the unreasonable behaviors such as stray movement, reverse movement and repetition of the request for the centrifuging, on the contrary, the evaluation parameter is sequentially lowered to "low" and "extremely low".

Each processing instrument collects, when requested for the delivery, the centrifuging or the analysis from the sample container 15, the reliability parameter information of the sample container 15 from the adjacent modules. This is evaluated to judge the reliability of the operation of the sample container 15. When the processing instrument makes its own schedule, it makes use of the reliability parameter and relies upon the sample container 15 to perform the desired processing preferentially if the parameter is "extremely high", for example. If "extremely low", on the contrary, the processing instrument rejects the request for the processing, which has been received, irrespective of the priority of the request and issues a caution to the terminal of the clinical laboratorian. Moreover, the processing instrument forcibly delivers the sample container 15 to the stocking instrument and stores the same in the stocking instrument so that the sample container 15 may not obstruct the operations of other sample containers and instruments. Thus, a highly reliable system operation can be obtained by ranking the sample containers according to the grades of behavior of the sample containers to determine the operating method and by rejecting the poorly reliable module.

As has been exemplified by the fifth to eighth embodiments, the issue of cooperation and concert between the modules, which have been understood as a difficult subject in the autonomous decentralized system of the prior art, are achieved by preventing the deadlock and operating the cooperative system by the contemplated executing operation of the plurality of sample containers, by improving the operation efficiency based on the priority and the weighing evaluation, by evading and rejecting poorly reliable modules by the reliability evaluation parameter of the modules.

Next, the third characteristic, the long-range optimizing operations for achieving the cooperative and concerted operations of the present automatic processing system, will be described in connection with ninth to thirteenth embodiments.

Ninth Embodiment

In the present embodiment, the communication mechanisms of the modules are extended, and even the information not pertinent or relevant to a module is stored in the memory mechanism of the module so that the information may be offered, if necessary, to other modules, like a "rumor". The traffic of communication is reduced and the communication is made efficient by the mechanism. Each module latches the information on other modules so that the long-range concert and cooperation can be achieved.

The present embodiment will be described in connection with the arrangement of FIG. 1. The accepting instrument 1 has functions to accept the plurality of sample containers and to send them out sequentially to the system. The numerous sample containers are placed in the accepting instrument 1 and participate in the system. The individual sample containers perceive the system arrangement and request the individual modules to offer the function information to acquire it.

The accepting instrument 1 transfers the request message to offer the function information addressed from the individual sample containers to the individual processing instruments, to the next instrument module, and transfers the message to report the functional information sent back from the individual processing instruments, to the individual sample containers. In addition to this fundamental operation, the accepting instrument 1 stores this report message in its own memory mechanism. If the same report is sent a predetermined number of times from one instrument, the accepting instrument 1 judges that the function information of the module hardly changes, and stores it. From now on, the accepting unit 1 interrupts, when it transfers the request message to offer the function information from each sample container to the module, the transfer based on its own judgment, and sends the function information of the module stored in the memory mechanism of its own module to the sample container, while clarifying that it is a representative reply, and stores the content and the time of the representative reply.

When each module reports the function information, a parameter indicating the probability of the information to change may be sent. On the basis of this parameter, the accepting instrument 1 can judge whether or not to make the representative reply. Each sample container tentatively uses the information from the accepting instrument 1 to execute the operations of determining the subsequent plan and making a reservation. Thanks to the representative reply, the path of the message is shortened to lower the amount of communication.

Each sample container executes the processing while confirming whether or not the representative reply information is correct, at important points such as branching points on the way of the delivery. If the reality has changed so that the information in the memory mechanism of the accepting instrument 1 has become outdated, the change in the information is detected by the confirming operation. The sample container, having detected the change in the information, sends a caution message stating the change in the information and containing a new valid information to the accepting instrument 1 that offered the old invalid information. The accepting instrument, having received the caution, updates the information in its own memory mechanism to a new valid information and judges that the information easily changes and stores it. Based on this, the accepting instrument will not make a representative reply on this information for a predetermined period after that. When and after the old information is offered to the sample container that returned the caution, whether or not the same old information has been offered to other modules is examined by the memory mechanism. If the old information is offered, a caution message that the information is invalid is sent to the modules. Alternatively, when the accepting instrument 1 starts the representative reply, it asks the module that it represents, to issue a caution when the information (on the module) happens to change. There may be adopted another mode in which the module having changed in the function information sends the caution message to all the modules in the system just after the change. Each module having received the caution message makes a new plan based upon the new valid information, if there is a plan based upon the old invalid information.

The present embodiment has been described by taking the representative reply as the function information, but a similar mechanism can be applied not only to the function information but also to the connection situation information or other information. This mechanism can flexibly update the information so that the path of the message that is mostly fixed and frequently repeated can be shortened to reduce the traffic of communication. One module acts as a proxy for a part of the functions of another module so that the system can be optimized in a long-range scale.

Tenth Embodiment

The present embodiment is extended from the ninth embodiment so that all the modules store the information such as the function information of other modules in the system.

Each module executes the connection situation perceiving operation to perceive the situation of connection of the entire system. The basic and mostly fixed function information is sent with an addressee address such as HCLAS to the entire system. The module belonging to the HCLAS receives the information as the message addressed thereto, and stores it separately for each sending module. These operations are executed by all the modules so that all the modules can perceive the function information of all the other modules. This information exchanging operation is executed at the set-up, or at the time of the change in the information, or periodically, so that the information is kept new and valid at all times, and the outdated information can be corrected.

This information exchange may also be executed such that each module sends the information to all the modules. Alternatively, the information may be circulated among the individual modules. In the latter case, one file may be circulated to pass around the information of all the modules by adopting the file type which has records the number of which is equal to the number of modules, the information of each module being contained in one record.

As a result of the above-described mechanism, the long-range information can be shared to reduce the traffic of communication concerning the rather static variable information. Incidentally, the module like the sample container has a small volume and in which the memory mechanism has a limited capacity can be excluded as an exception from the objects of the aforementioned operations to spare the memory capacity and reduce the volume and weight. In this case, the function information of the entire system can be acquired by a method where the instrument modules belonging to the processing instrument (PRC) sends the function information by using the addressee address as the PRC, and the sample container inquires the instrument module close thereto.

Eleventh Embodiment

In the present embodiment, the module leaves its partial function to another module so that this module acts as a proxy for the function. In the foregoing embodiments, each sample container searches the module necessary for each procedure, when it requests each processing instrument to confirm the processing executing function, to acquire the reservation and to execute the processing, and determines the combination of the necessary modules for executing the procedure. In the present embodiment, the plurality of modules are combined to a superclass module for executing the processing operation.

A description will be made by taking the arrangement of FIG. 1 as an example. The modules 2, 8, 3 and 4 and the modules 5, 9, 6 and 7 perceive, in the adjacent situation perceiving operation at the set-up, that they are classified as the delivery instruments (DEL). The information sharing as described in the previous two embodiments is carried out by each continuous section of the modules such as 2, 8, 3 and 4 so that each section is prepared to function unitedly. The delivery instrument modules belonging to each section exchange function transferring messages with each other, and make a contract to function as an integral delivery instrument class.

Each module in the integral section issues by itself a new ID number composed of a series of ID numbers of the members of the section and starts a function as a one-class module (superclass module). The superclass module informs the surrounding modules that it has become a superclass module, and executes the adjacent situation perceiving operation.

Figure 18:
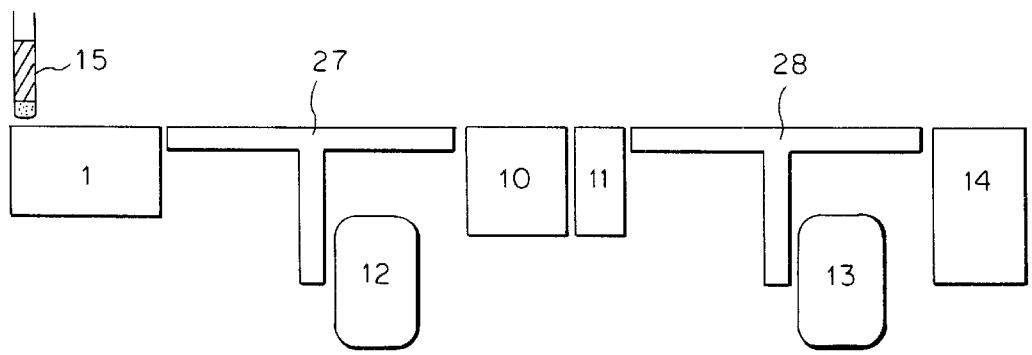
FIG. 18 is a schematic arrangement diagram of an automatic processing system including superclass modules 27 and 28 of an eleventh embodiment.

FIG. 18 is a schematic arrangement diagram showing an automatic processing system including superclass modules. The modules 2, 8, 3 and 4 and the modules 5, 9, 6 and 7 (as shown in FIG. 1) respectively function as virtual superclass modules 27 and 28 belonging to the delivery instrument (DEL.PRC.HCLAS).

If the sample container requests each module in a superclass to offer the function information, the modules do not individually reply, but one module replies the function information of the superclass module composed of the same modules as above. The module having replied executes the delivery over itself and other modules in concert with other modules. If the delivery is made from the first module to another module in the superclass module, the content of request for delivery is transmitted to the second module. As a result, the sample container is delivered in the superclass module even without having to send requests from the sample container to the other modules individually.

Since the plurality of modules are capsulated into the superclass module, the details of the modules constituting the class are shielded from the outside so that the modules operate as the superclass module of the delivery instrument class having apparently a simple arrangement and function. The individual modules are capsulated as a superclass, so that the system arrangement can be simplified, when viewed from the sample container, to effect a simple control.

Figure 19:
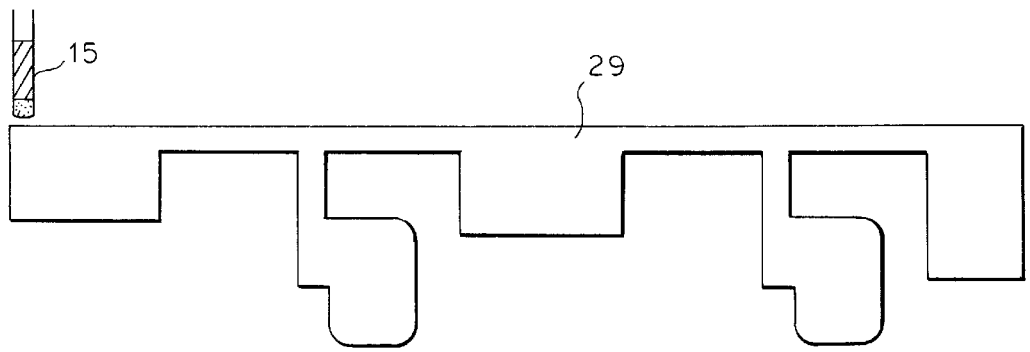
FIG. 19 is a schematic arrangement diagram of another automatic processing system including the superclass module 29 of the eleventh embodiment.

In the case the information processor and memory mechanism of each processing instrument module have greater abilities, the modules can not only form the superclass according to the large classification of the system but also be capsulated as a higher ranked class. FIG. 19 shows another automatic processing system including a superclass module composed of the same modules above. The superclass module 29 of the processing instrument (PRC.HCLAS) has all the processing functions such as the accepting, delivering, centrifuging, aliquoting, analyzing and stocking operations. The superclass module 29 has no central processing instrument but realizes the efficient operations as a whole in cooperation and concert among the individual processing instruments. The superclass module 29 is one ultimate embodiment of the autonomous decentralized automatic processing system.

Twelfth Embodiment

The present embodiment will be described of the case in which the sample container has no information processor.

The communication mechanism of the sample container preferably has a simple arrangement. If the memory mechanism is an electric memory, for example, the communication mechanism may be a bundle of cables or a wiring pattern and connection terminals for connecting the memory mechanism and the outside. The memory mechanism may be a magnetic tape or bar codes.

The information such as the list of items to be analyzed, requested by the doctor, is stored in the memory mechanism of the sample container by using the connection terminals, or the magnetic recording mechanism disposed at the terminal of the doctor, or the communication mechanism such as a bar code writer. Each processing instrument module having accepted the sample container reads out the information by the connection terminals, a magnetic reading mechanism, or a bar code reader. In the present embodiment, each processing instrument module acts as a proxy for the operations of the information processor of the sample container in the foregoing other embodiments. When the sample container is to be delivered to the next module, the information representing the previous execution procedure is written through the communication mechanism in the memory mechanism in the sample container and is sent to the next module. Alternatively, the information may be sent to the next module in synchronism with the delivery of the sample container.

The present embodiment needs no information processor in the sample container, so that its system arrangement can be simplified to lower the production cost.

Thirteenth Embodiment

In the present embodiment, the sample container has the information processor, the memory mechanism and the communication mechanism as in the first to eleventh embodiments, but the processing instrument may be controlled by the central processing instrument. The processing instrument may have the information processor, the memory mechanism and the communication mechanism, but the central processing instrument need not control the processing instrument at all times. If the present autonomous decentralized control mode comes into an unexpected deadlock, or at the time of starting up a new system, debugging is performed, or the operation is checked, the autonomous decentralized control can be canceled and the central processing is forcedly conducted. This can be a backup system to restore to a conventional way of operation. In this case, each processing instrument module has an autonomous decentralized control software, and a conventional central processing control software, and a hardware or software for switching between those two operation modes.

In the present embodiment, the sample container is stored with the processing purpose and means such as the list of requested items to be analyzed and the abstract processing procedure.

The effects to be produced by the arrangement of the present embodiment will be enumerated in the following. By separating the sample information and the information for operating the processing instrument, the softwares can be easily made and managed. The information processings for the sample are distributed to the individual sample containers, so that the parallel information processing can be achieved. The real time processability and responsiveness of the information processings, such as the evaluation of the operation of each sample container are improved. A more extensive processing per unit time can be achieved to realize a higher grade processing. By capsulating the sample container and the information, the management of the information on the sample can be facilitated to prevent the dissipation of the information, so that the reliability can be improved to reduce the traffic of communication. The software for the sample container can be singly debugged.

Although all the foregoing embodiments which have been described are the application to the clinical diagnostic analysis, the application of the present invention is not limited thereto but can be extended to the food analysis, the environmental analysis and the resources investigation analysis. Further, the present invention can be applied not only to the automation of the chemical component analysis such as the clinical analysis but also to the physical analysis. The present invention can be further applied to the manufacture automation in factories, the collection/delivery of goods or parts, or the system including the objects to be processed and the processing instrument such as a hospital patient guidance system or an automatic automobile driving system. In these cases, what corresponds to the sample container in the foregoing embodiments is an object (e.g., a material or a part constituting a product, a package, a portable terminal for patients, or an automobile) to be processed, or a container or a tag. What corresponds to each processing instrument of the foregoing embodiments is a processor (e.g., a group of automatic manufacture apparatus or a group of conveyor apparatus in a factory, a group of good collecting/delivering apparatus, a patient guidance system or an automatic car-driving aiding system). By the substitution the system arrangement of the present invention can be applied, providing similar effects.

The present invention is arranged, as has been described hereinbefore, so that the system can be easily constructed and corrected. Moreover, the change in the arrangement can be flexibly coped with to prevent a partial failure from propagating to another. Still moreover, the ability of the system at a time can be maximized to optimize the processing.

While the present invention has been described in detail and pictorially in the accompanying drawings it is not limited to such details since many changes and modifications recognizable to those of ordinary skill in the art may be made to the invention without departing from the spirit and the scope thereof.

We claim:

1. An automatic processing system, comprising:
   a plurality of processing instruments; and
   at least one object to be processed by said plurality of processing instruments,
   wherein each of said processing instruments and said object comprises:
      an information processor for operating each of said processing instruments and said object, autonomously in parallel,
      a memory for storing a software for cooperative concerted operations, and
      a communication unit for exchanging information between each of said processing instruments and said object;
   wherein said object determines a processing procedure based on information concerning said processing instruments obtained from said processing instruments,
   wherein said processing instruments process said object based on said processing procedure determined by said object, and
   wherein said automatic processing system as a whole functions as an autonomous decentralized processing system.

2. An automatic processing system according to claim 1, wherein said object is a sample container containing a sample, and
   wherein said processing procedure includes at least one of an accepting operation, a temporary stocking operation, a delivery operation, a shunting operation, a storing operation, a centrifuging operation, an uncapping operation, an aliquoting operation, a sample analyzing operation, and a processing operation for analysis.

3. An automatic processing system according to claim 2, wherein said information represents an arrangement of said processing instruments.

4. An automatic processing system according to claim 2, wherein said information represents functions of said processing instruments.

5. An automatic processing system according to claim 2, wherein said information represents an operation schedule for said processing instruments to process said sample container.

6. An automatic processing system according to claim 2, wherein said processing instruments are classified according to individual functions, and
   wherein said sample container stores an abstract processing procedure that is a combination of said functions.

7. An automatic processing system according to claim 6, wherein said sample container determines said processing procedure based on said abstract processing procedure and said information.

8. An automatic processing system according to claim 2, wherein said plurality of processing instruments are classified according to individual functions.

9. An automatic processing system, comprising:
   a plurality of processing instruments; and
   at least one object to be processed by said plurality of processing instruments,
   wherein each of said processing instruments comprises:
      an information processor for operating each of said processing instruments, autonomously in parallel,
      a memory for storing a software for cooperative concerted operations, and
      a communication unit for exchanging information between each of said processing instruments;
   wherein said object stores an abstract processing procedure which represents processing to be performed on said object,
   wherein said processing instruments process said object based on said abstract processing procedure obtained from said object, and
   wherein said automatic processing system as a whole functions as an autonomous decentralized processing system.

10. An automatic processing system according to claim 9, wherein said object is a sample container containing a sample, and
    wherein said processing procedure includes at least one of an accepting operation, a temporary stocking operation, a delivery operation, a shunting operation, a storing operation, a centrifuging operation, an uncapping operation, an aliquoting operation, a sample analyzing operation, and a processing operation for analysis.

11. An automatic processing system according to claim 10, wherein said processing instruments are classified according to individual functions, and wherein said sample container stores an abstract processing procedure that is a combination of said individual functions.

12. An automatic processing system according to claim 10, wherein said plurality of processing instruments are classified according to individual functions.

13. An automatic processing systems comprising:
a plurality of processing instruments; and
at least one object to be processed by said plurality of processing instruments,
wherein each of said processing instruments and said object comprises:
an information processor for operating each of said processing instruments and said object, autonomously in parallel,
a memory for storing a software for cooperative concerted operations, and
a communication unit for exchanging information between each of said processing instruments and said object;
wherein said object stores an abstract processing procedure which represents processing to be performed on said object,
wherein said object determines a processing procedure based on information of said processing instruments obtained from said processing instruments and said abstract processing procedure,
wherein said processing instruments process said object based on said processing procedure determined by said object, and
wherein said automatic processing system as a whole functions as an autonomous decentralized processing system.

14. An automatic processing system according to claim 13, wherein said object is a sample container containing a sample, and
wherein said processing procedure includes at least one of an accepting operation, a temporary stocking operation, a delivery operation, a shunting operation, a storing operation, a centrifuging operation, an uncapping operation, an aliquoting operation, a sample analyzing operation, and a processing operation for analysis.

15. An automatic processing system according to claim 14, wherein said information represents an arrangement of said processing instruments.

16. An automatic processing system according to claim 14, wherein said information represents functions of said processing instruments.

17. An automatic processing system according to claim 14, wherein said information represents an operation schedule for said processing instruments to process said sample container.

18. An automatic processing system according to claim 14, wherein said processing instruments are classified according to individual functions, and
wherein said processing procedure is described as the combination of said functions.

19. An automatic processing system as set forth in claim 14, wherein said sample container and said processing instruments include connection apparatus which changes its individual states of connection.

20. An automatic processing system according to claim 14,
wherein said processing instruments and said sample container each store identification information including an ID number or a model identification code in said memory,
wherein said information is the one that is acquired through communications using said communication units between said processing instruments and said sample container, and said information includes information concerning said sample container,
wherein said sample container determines a processing procedure based on said information acquired, and
wherein said processing instruments process said sample container based on said processing procedure.

21. An automatic processing system according to claim 14,
wherein said processing instruments and said sample container each store identification information including an ID number or a model identification code in said memory,
wherein said information is the one that is acquired through communications with a predetermined counterpart using said communication units between said processing instruments and said sample container, and said information is information concerning said predetermined counterpart,
wherein said sample container determines the processing procedure based on said information acquired, and
wherein said processing instruments process said sample container based on said processing procedure.

22. An automatic processing system according to claim 14, wherein said plurality of processing instruments evaluate their reliabilities mutually, and
wherein said sample container selects one of said processing instruments based on a result of said evaluation so that the selected processing instrument processes said sample container.

23. An automatic processing system according to claim 14, wherein said processing instruments evaluate reliability of said sample container, and
wherein said processing instruments reject said sample container based on a result of said evaluation.

24. An automatic processing system comprising:
a plurality of processing instruments; and
at least one obiect to be processed by said plurality of processing instruments,
wherein each of said processing instruments and said obiect comprises:
an information processor for operating each of said processing instruments and said object, autonomously in parallel,
a memory for storing a software for cooperative concerted operations, and
a communication unit for exchanging information between each of said processing instruments and said object;
wherein said object stores an abstract processing procedure which represents processing to be performed on said objects,
wherein said object determines a processing procedure based on information on said processing instruments obtained from said processing instruments and said abstract processing procedure,
wherein said processing instruments process said object based on said processing procedure determined by said object,
wherein said object is a sample container containing a sample,
wherein said sample container stores information representing a deadline for processing in said memory, wherein said plurality of processing instruments process said sample container based on said information representing said deadline, wherein said processing procedure includes at least one of an accepting operation, a temporary stocking operation, a delivery operation, a shunting operation, a storing operation, a centrifuging operation, an uncapping operation, an aliquoting operation, a sample analyzing operation, and a processing operation for sample analysis, and wherein said automatic processing system as a whole functions as an autonomous decentralized processing system.

25. An automatic processing system comprising:

a plurality of processing instruments; and at least one object to be processed by said plurality of processing instruments, wherein each of said processing instruments and said object comprises:

an information processor for operating each of said processing instruments and said object, autonomously in parallel, a memory for storing a software for cooperative concerted operations, and a communication unit for exchanging information between each of said processing instruments and said obiect;

wherein said object stores an abstract processing procedure which represents processing to be performed on said object, wherein said obiect determines a processing procedure based on information on said processing instruments obtained from said processing instruments and said abstract processing procedure, wherein said processing instruments process said object based on said processing procedure determined by said object, wherein said object is a sample container containing a sample, wherein said information includes information of a first predetermined sample container of said sample containers, wherein a second predetermined sample container of said sample containers acquires information from other containers of said processing instruments or a third predetermined sample container of said sample containers so that said second predetermined sample container determines a processing procedure based on said information and so that said processing instruments process said second predetermined sample container based on said processing procedure, wherein said processing procedure includes at least one of an accepting operation, a temporary stocking operation, a delivery operation, a shunting operation, a storing operation, a centrifuging operation, an uncapping operation, an aliquoting operation, a sample analyzing operation, and a processing operation for sample analysis, and wherein said automatic processing system as a whole functions as an autonomous decentralized processing system.

26. An automatic processing system, comprising:

a plurality of processing instruments; and at least one object to be processed by said plurality of processing instruments, wherein each of said processing instruments and said object comprises:

an information processor for operating each of said processing instruments and said object, autonomously in parallel, a memory for storing a software for cooperative concerted operations, and a communication unit for exchanging information between each of said processing instruments and said object;

wherein said object stores an abstract processing procedure which represents processing to be performed on said object wherein said object determines a processing procedure based on information on said processing instruments obtained from said processing instruments and said abstract processing procedure, wherein said processing instruments process said object based on said processing procedure determined by said object, wherein said object is a sample container containing a sample, wherein said processing instruments or said sample container acts as a proxy for the other processing instruments or the other sample containers, wherein said processing procedure includes at least one of an accepting operation, a temporary stocking operation, a delivery operation, a shunting operation, a storing operation, a centrifuging operation, an uncapping operation, an aliquoting operation, a sample analyzing operation, and a processing operation for sample analysis, and wherein said automatic processing system as a whole functions as an autonomous decentralized processing system.

27. A method of processing at least one object in an automatic processing system which includes a plurality of processing instruments, comprising the steps of:

storing a software for cooperative concerted operations in a memory of each of said processing instruments and said obiect, communicating for exchanging information between each of said processing instruments and said object;

determining in said object a processing procedure to be performed on said object by said processing instruments based on information concerning said processing instruments obtained from said processing instruments; and processing by said processing instruments said object based on said processing procedure determined by said object, wherein each of said processing instruments and said obiect is operated, autonomously in parallel, by an information processor in each of said processing instruments and said obiect, and said automatic processing system as a whole functions as an autonomous decentralized processing system.

28. A method according to claim 27, wherein said information represents an arrangement of said processing instruments.

29. A method according to claim 27, wherein said information represents functions of said processing instruments.

30. A method according to claim 27, wherein said information represents an operation schedule for said processing instruments to process said object.

31. A method according to claim 27, wherein said object stores an abstract processing procedure that is a combination of functions of said processing instruments.

32. A method according to claim 31, wherein said object determines said processing procedure based on said abstract processing procedure and said information.

33. A method according to claim 27, wherein said object is a sample container containing a sample.

34. A method of processing at least one object in an automatic processing system which includes a plurality of processing instruments, comprising the steps of:

storing a software for cooperative concerted operations in a memory of each of said processing instruments and said object, storing in said object an abstract processing procedure which represents processing to be performed on said object;

communicating for exchanging information between each of said processing instruments and said object;

determining, in said object, a processing procedure based on information of said processing instruments obtained from said processing instruments and said abstract processing procedure stored in said object; and processing, in said processing instruments, said object based on said processing procedure determined by said object, wherein each of said processing instruments and said object is operated, autonomously in parallel, by an information processor in each of said processing instruments and said object, and said automatic processing system as a whole functions as an autonomous decentralized processing system.

* * * * *